United States Patent
Shachar et al.

(10) Patent No.: US 10,066,014 B2
(45) Date of Patent: Sep. 4, 2018

(54) ANTI CD84 ANTIBODIES, COMPOSITIONS COMPRISING SAME AND USES THEREOF

(71) Applicant: Yeda Research and Development Co. Ltd., Rehovot (IL)

(72) Inventors: Idit Shachar, Ramat-Gan (IL); Inbal Binsky, Rehovot (IL); Ayelet Marom, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/116,276

(22) PCT Filed: Feb. 5, 2015

(86) PCT No.: PCT/IL2015/050133
§ 371 (c)(1),
(2) Date: Aug. 3, 2016

(87) PCT Pub. No.: WO2015/118538
PCT Pub. Date: Aug. 13, 2015

(65) Prior Publication Data
US 2017/0260270 A1    Sep. 14, 2017

Related U.S. Application Data

(60) Provisional application No. 61/936,361, filed on Feb. 6, 2014.

(51) Int. Cl.
| | | |
|---|---|---|
| *C07K 16/28* | (2006.01) | |
| *G01N 33/574* | (2006.01) | |
| *C07K 16/30* | (2006.01) | |
| *G01N 33/50* | (2006.01) | |
| *A61K 39/395* | (2006.01) | |

(52) U.S. Cl.
CPC ...... *C07K 16/2806* (2013.01); *C07K 16/3061* (2013.01); *G01N 33/5011* (2013.01); *G01N 33/57426* (2013.01); *C07K 2317/31* (2013.01); *C07K 2317/33* (2013.01); *C07K 2317/73* (2013.01); *C07K 2317/76* (2013.01); *G01N 2333/70507* (2013.01); *G01N 2500/10* (2013.01)

(58) Field of Classification Search
CPC ..... C07K 16/28; A61K 39/395; G01N 33/574
USPC .......................... 530/388.1; 424/139.1, 141.1
See application file for complete search history.

(56) References Cited

U.S. PATENT DOCUMENTS

| | | | |
|---|---|---|---|
| 8,686,121 B2 * | 4/2014 | Shachar | C07K 14/70596 435/334 |
| 9,109,029 B2 * | 8/2015 | Shachar | C07K 14/70596 |
| 2003/0049618 A1 | 3/2003 | Ruben et al. | |
| 2003/0175858 A1 | 9/2003 | Ruben et al. | |
| 2005/0025789 A1 | 2/2005 | Nieland et al. | |
| 2005/0027114 A1 | 2/2005 | Kuo et al. | |
| 2014/0147451 A1 | 5/2014 | Shachar et al. | |
| 2015/0344972 A1 | 12/2015 | Shachar et al. | |

FOREIGN PATENT DOCUMENTS

| | | |
|---|---|---|
| WO | WO 01/55336 | 8/2001 |
| WO | WO 2010/035259 | 4/2010 |
| WO | WO 2015/118538 | 8/2015 |

OTHER PUBLICATIONS

Official Action dated Jul. 27, 2017 From the US Patent and Trademark Office Re. U.S. Appl. No. 14/827,337. (17 pages).
Communication Pursuant to Article 94(3) EPC dated Jul. 24, 2017 From the European Patent Office Re. Application No. 09740767.0. (8 Pages).
Communication Pursuant to Article 94(3) EPC dated Jul. 24, 2017 From the European Patent Office Re. Application No. 15709365.9. (6 Pages).
Communication Pursuant to Article 94(3) EPC dated Jun. 3, 2015 From the European Patent Office Re. Application No. 09740767.0.
Communication Relating to the Results of the Partial International Search dated Feb. 2, 2010 From the International Searching Authority Re.: Application No. PCT/IL2009/000919.
International Preliminary Report on Patentability dated Apr. 7, 2011 From the International Bureau of WIPO Re. Application No. PCT/IL2009/000919.
International Preliminary Report on Patentability dated Aug. 18, 2016 From the International Bureau of WIPO Re. Application No. PCT/IL2015/050133.
International Search Report and the Written Opinion dated Apr. 6, 2010 From the International Searching Authority Re.: Application No. PCT/IL2009/000919.
International Search Report and the Written Opinion dated May 20, 2015 From the International Searching Authority Re. Application No. PCT/IL2015/050133.
Office Action dated Jun. 29, 2014 From the Israel Patent Office Re. Application No. 228595 and Its Translation Into English.
Official Action dated Oct. 21, 2014 From the US Patent and Trademark Office Re. U.S. Appl. No. 14/172,926.
Official Action dated Jun. 24, 2014 From the US Patent and Trademark Office Re. U.S. Appl. No. 14/172,926.
Bando et al. "Expression of Macrophage Migration Inhibitory Factor in Human Breast Cancer: Association With Nodal Spread", Japanese Journal of Cancer Research, 93: 389-396, Apr. 2002.
Becker-Herman et al. "CD74 Is a Member of the Regulated Intramembrane Proteolysis-Processed Protein Family", Molecular Biology of the Cell, 16: 5061-5069, Nov. 2005.

(Continued)

*Primary Examiner* — Yan Xiao

(57) ABSTRACT

An isolated antibody comprising an antigen recognition domain which specifically binds CD84 and
(i) down regulates the anti-apoptotic activity of stromal cells on chronic lymphocytic leukemia (CLL) cells; and/or
(ii) induces mobilization of CLL cells from the bone marrow.
Also provided are antibodies comprising antigen recognition domains comprising complementarity determining regions as indicated and uses thereof.

11 Claims, 13 Drawing Sheets
(5 of 13 Drawing Sheet(s) Filed in Color)

Specification includes a Sequence Listing.

(56) References Cited

OTHER PUBLICATIONS

Binsky et al. "IL-8 Secreted in a Macrophage Migration-Inhibitory Factor- and CD74-Dependent Manner Regulates B Cell Chronic Lymphocytic Leukemia Survival", Proc. Natl. Acad. Sci. USA, PNAS, 104(33): 13408-13413, Aug. 14, 2007.
Brown et al. "2B4, the Natural Killer and T Cell Immunoglobulin Superfamily Surface Protein, Is a Ligand for CD48", Journal of Experimental Medicine, XP002574396, 188(11): 2083-2090, Dec. 7, 1998. p. 2084, col. 1, § 2, Fig.3, p. 2086, 2088.
Calpe et al. "The SLAM and SAP Gene Families Control Innate and Adaptive Immune Responses", Advances in Immunology, 97(Chap. 4): 177-250, 2008.
De La Fuente et al. "CD84 Leukocyte Antigen Is a New Member of the Ig Superfamily", Blood, XP002925318, 90(6): 2398-2405, Sep. 15, 1997.
Martin et al. "CD84 Functions As a Homophilic Adhesion Molecule and Enhances IFN-Gamma Secretion: Adhesion Is Mediated by Ig-Like Domain 1[1]", The Journal of Imunology, XP055187840, 167(7): 3668-3676, Oct. 1, 2001.
Matza et al. "Invariant Chain Induces B Cell Maturation by Activating a TAF[II]105-NF-KB-Dependent Transcription Program", The Journal of Biological Chemistry, 276(29): 27203-27206, Jul. 20, 2001.
Matza et al. "Invariant Chain Induces B Cell Maturation in a Process That Is Independent of Its Chaperonic Activity", Proc. Natl. Acad. Sci. USA, PNAS, 99(5): 3018-3023, Mar. 5, 2002.
Matza et al. "Invariant Chain, A Chain of Command", Trends in Immunology, 24(5): 264-268, May 2003.
Matza et al. "Invariant Chain-Induced B Cell Differentiation Requires Intramembrane Proteolytic Release of the Cytosolic Domain", Immunity, 17: 549-560, Nov. 2002.
Mizue et al. "Quantitation of Macrophage Migration Inhibitory Factor (MIF) Using the One-Step Sandwich Enzyme Immunosorbent Assay: Elevated Serum MIF Concentrations in Patients With Autoimmune Diseases and identification of MIF in Erythrocytes", International Journal of Molecular Medicine, 5(4): 397-403, 2000.
Narni et al. "HLA-DR-Associated Invariant Chain Is Highly Expressed in Chronic Lymphocytic Leukemia", Blood, 68: 372-377, 1986.
NCBI "Leukemia, Lynphocytic, Chronic, B-Cell", Medical Subject Headings, MeSH, NCBI, 3 P., 2008 (1989).
Nishihira et al. "Macrophage Migration Inhibitory Factor (MIF). Its Potential Role in Tumor Growth and Tumor-Associated Angiogenesis", Annals of the New York Academy of Sciences, 995: 171-182, 2003.
Palou et al. "Genomic Characterization of CD84 Reveals the Existence of Five Isoforms Differing in Their Cytoplasmic Domains", Tissue Antigens, XP002739389, 55(2): 118-127, Feb. 2000.
Shanchar et al. "Requirement for Invariant Chain in B Cell Maturation and Function", Science, 274(5284): 106-108, Oct. 4, 1996.
Tangye et al. "CD84 Is Up-Regulated on a Major Population of Human Memory B Cells and Recruits the SH2 Domain Containing Proteins SAP and EAT-2", European Journal of Immunology, XP002739388, 32(6): 1640-1649, Jun. 2002.
Yan et al. "Structure of CD84 Provides Insight Into SLAM Family Function", Proceedings of the National Academy of Sciences, USA, XP002563816, 104(25): 10583-10588, Jun. 19, 2007. p. 10588.
Zaiss et al. "CD84 Expression on Human Hematopoietic Progenitor Cells", Experimental Hematology, XP003025697, 31(9): 798-805, Sep. 1, 2003.
Official Action dated Jan. 16, 2018 From the US Patent and Trademark Office Re. U.S. Appl. No. 14/827,337. (20 pages).
Advisory Action Before the Filing of an Appeal Brief dated Apr. 25, 2018 From the US Patent and Trademark Office Re. U.S. Appl. No. 14/827,337. (3 pages).

* cited by examiner

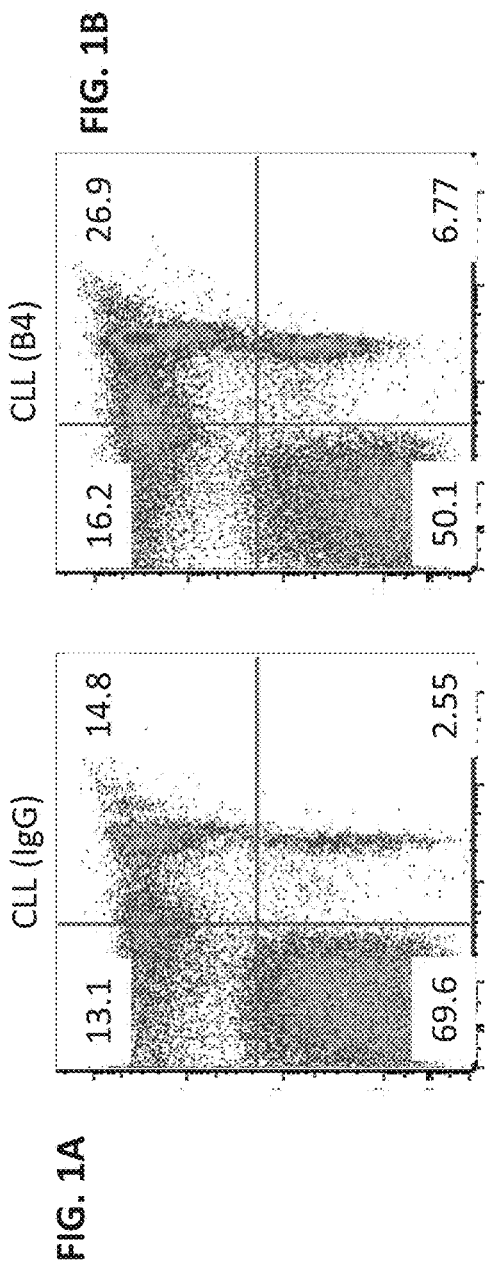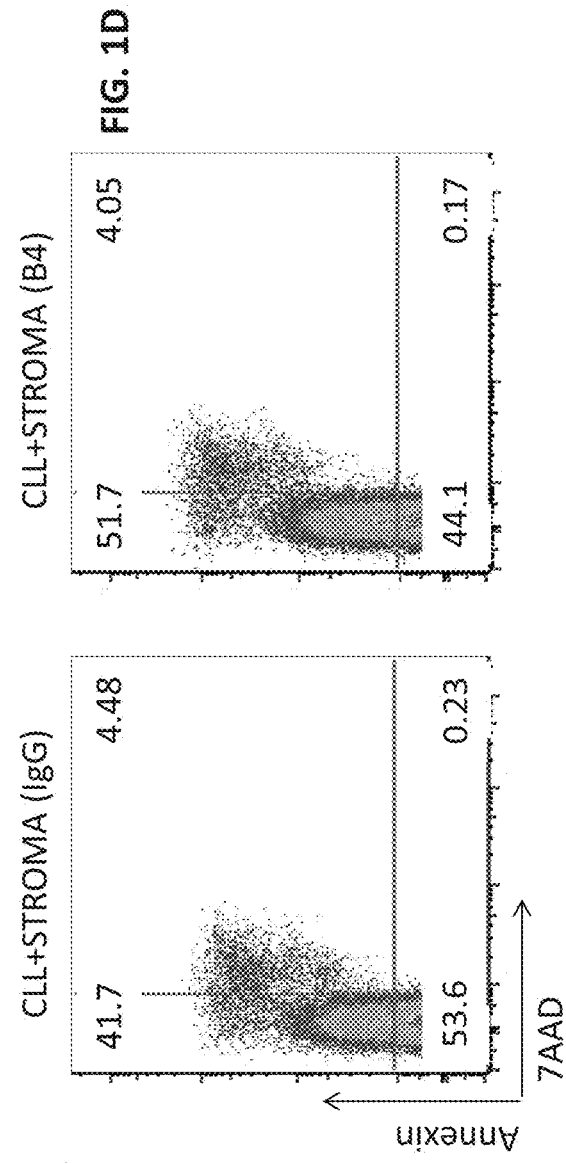

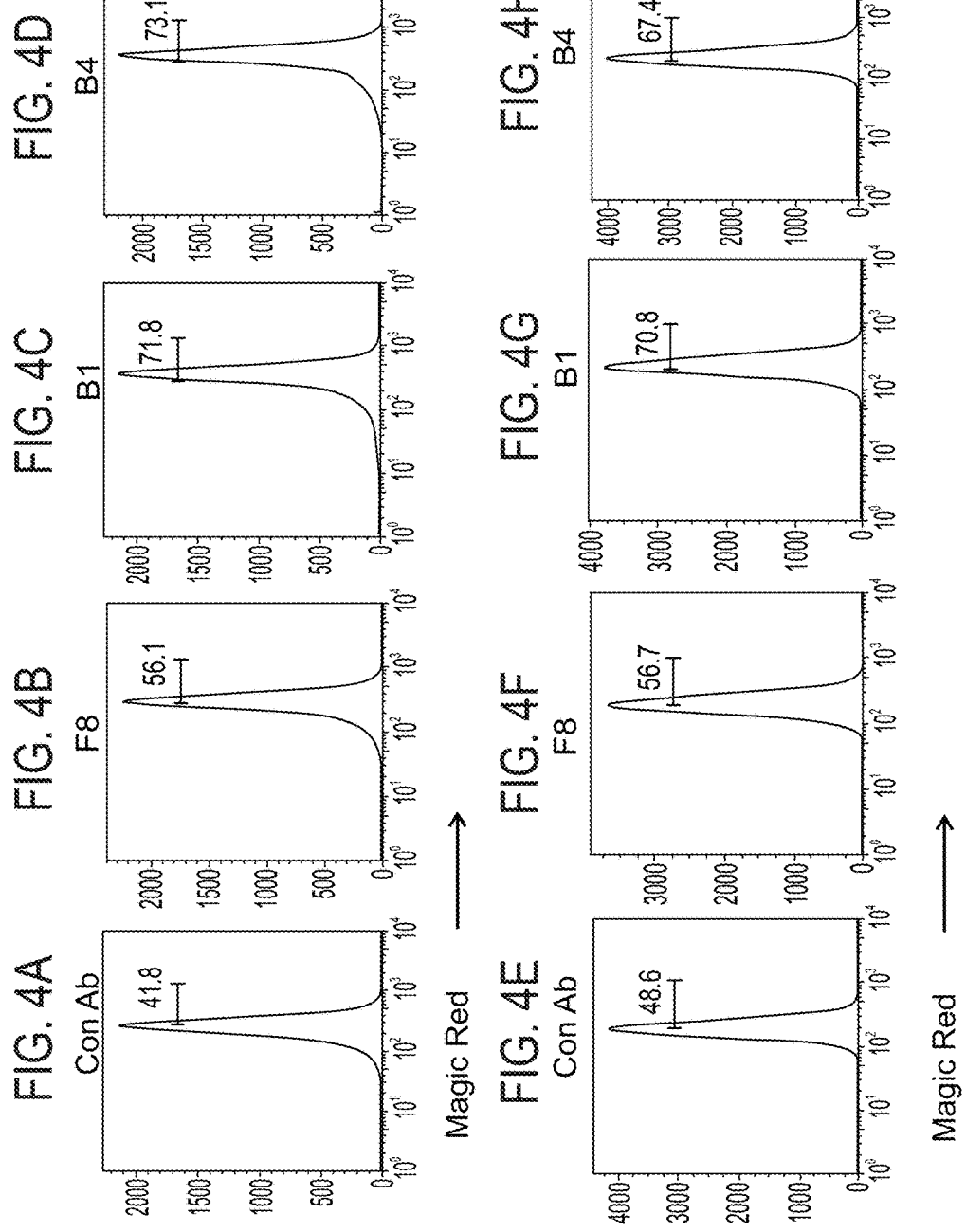

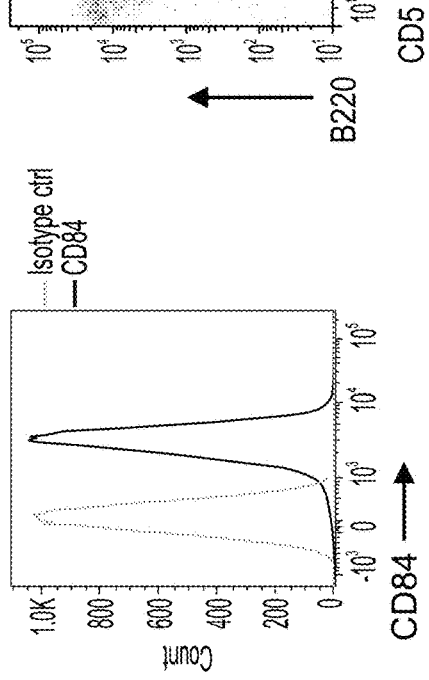
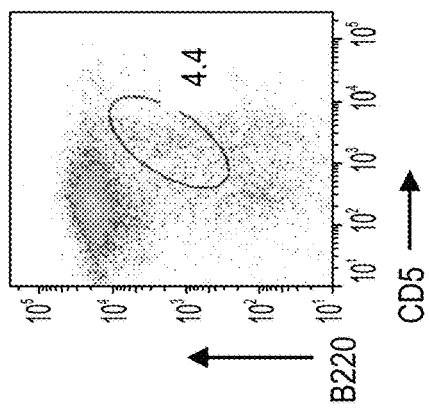
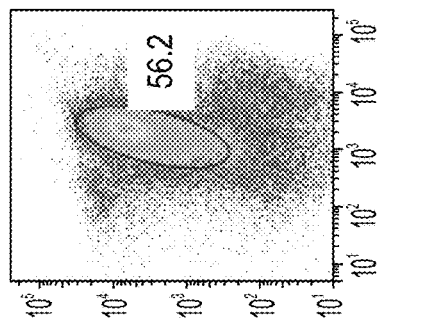
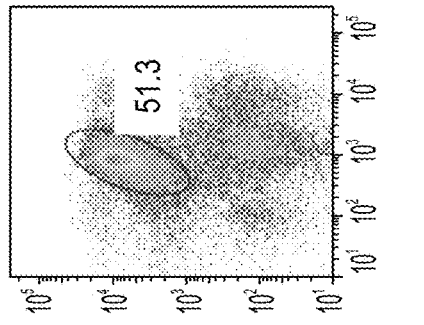

IgG2a 5 μg/mL

B1 5 μg/mL

B4 5 μg/mL 6 months

IgG2a 5 μg/mL

B1 5 μg/mL

B4 5 μg/mL 11 month

IgG2a 20 μg/mL

B1 20 μg/mL

B4 20 μg/mL 18 months

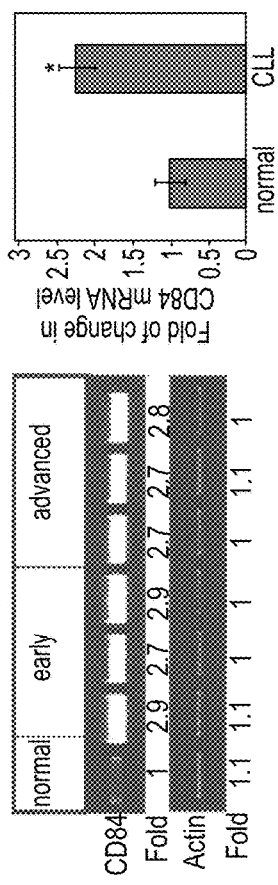
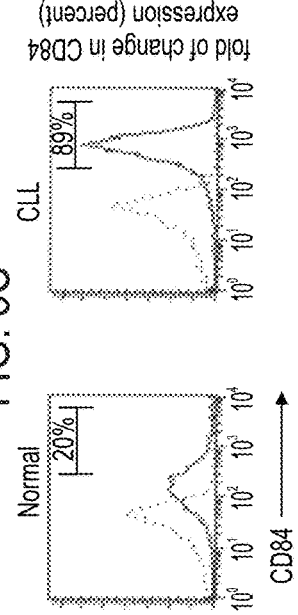
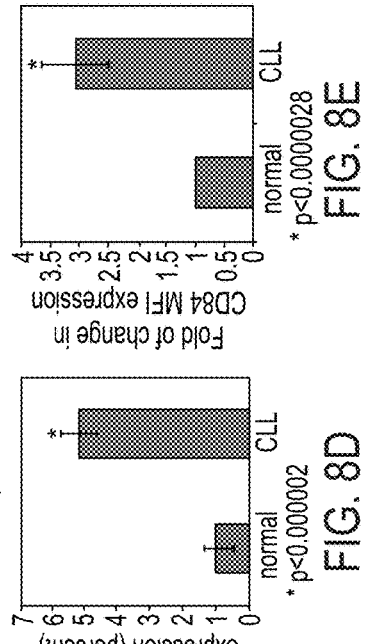
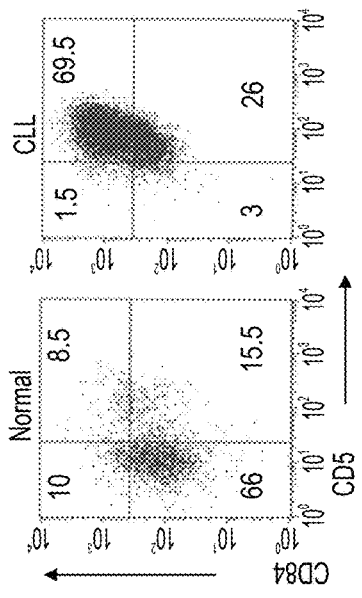

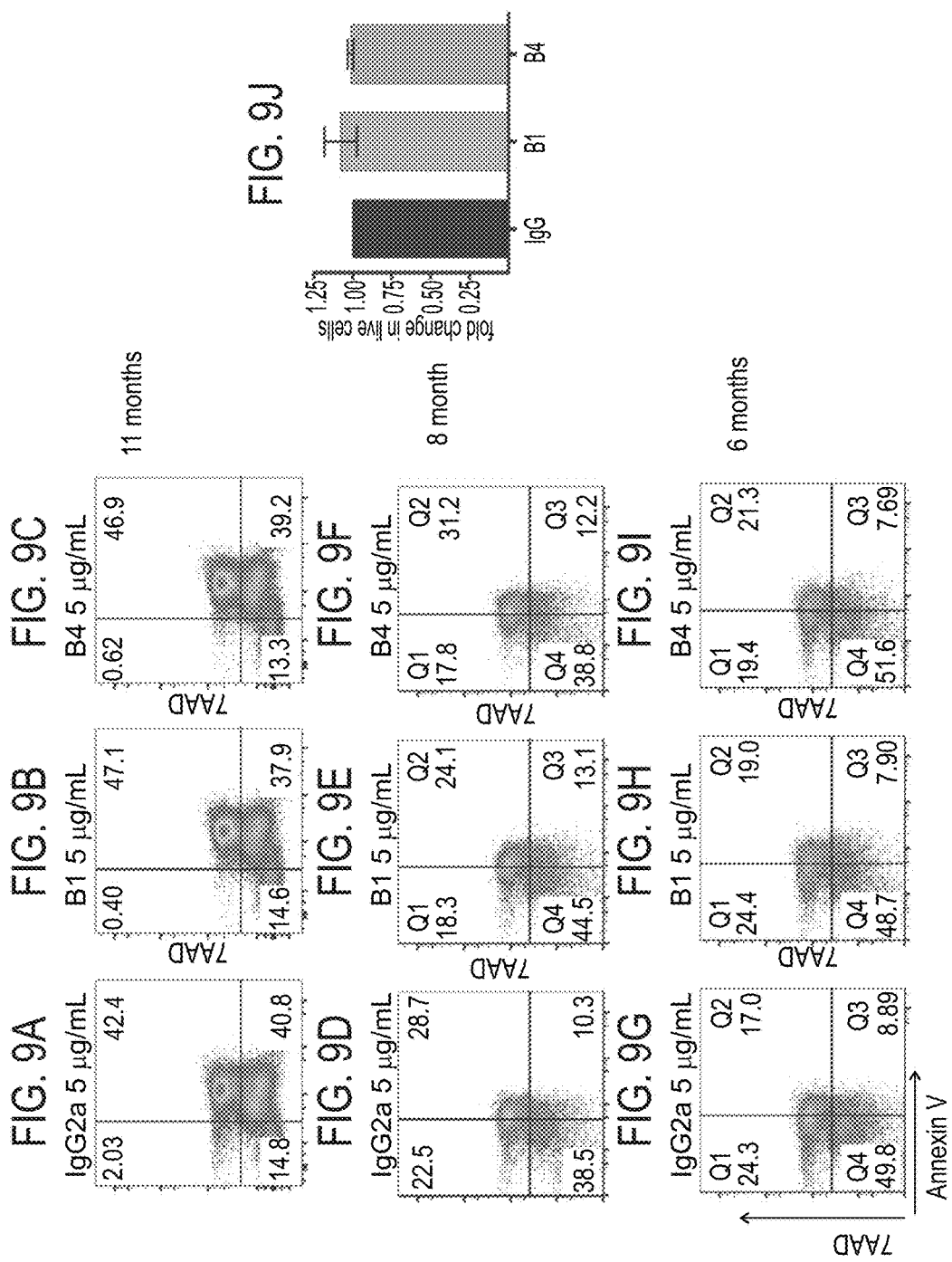

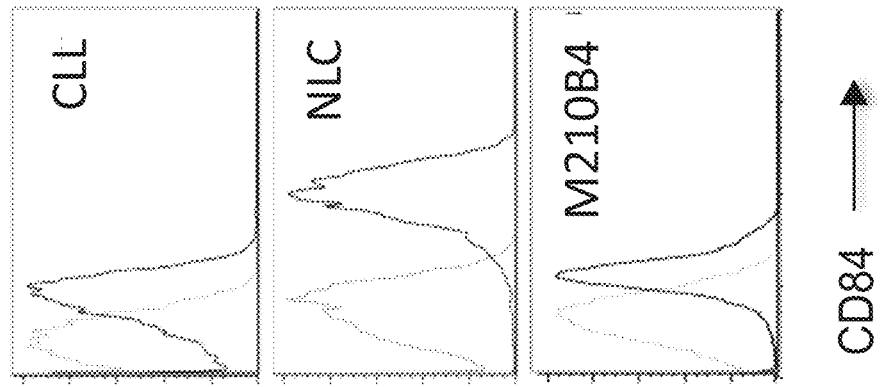
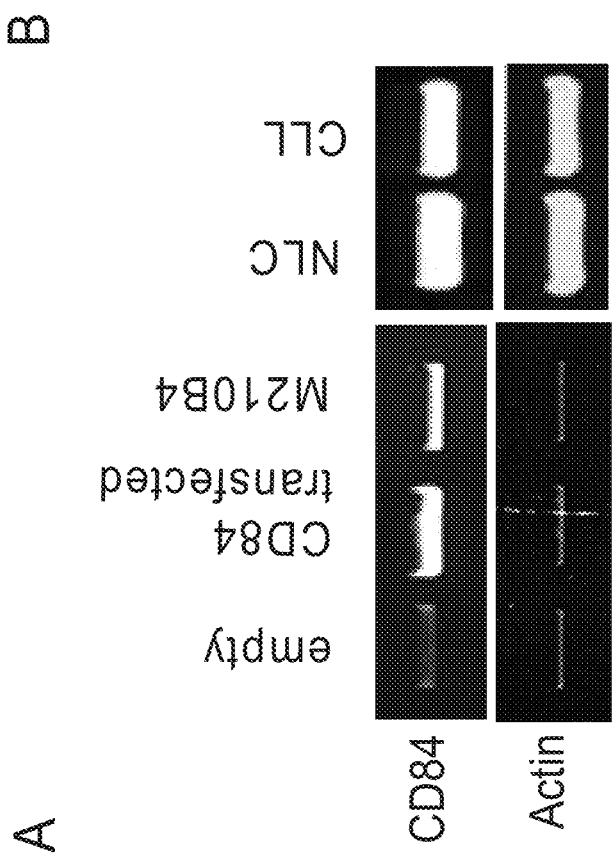
FIG. 10A
FIG. 10B

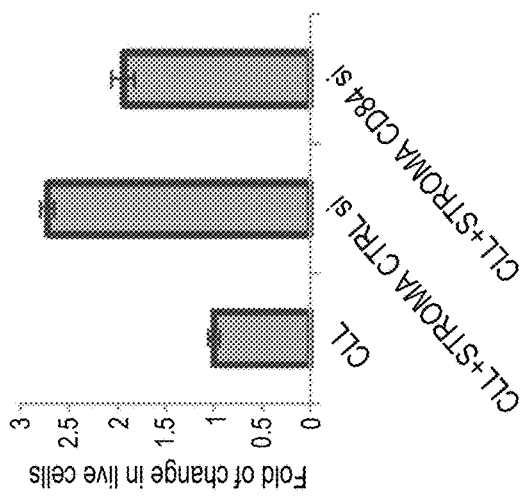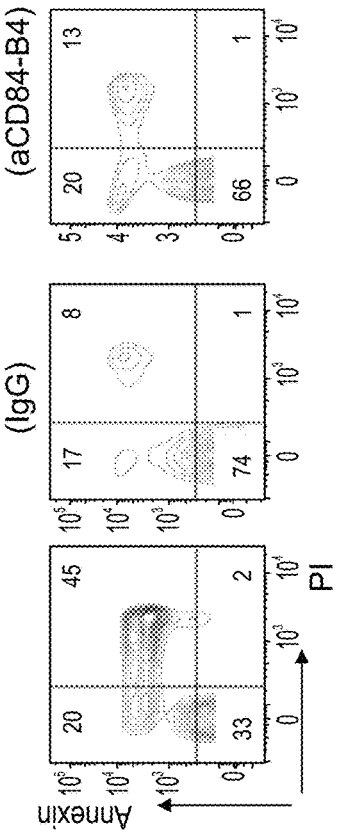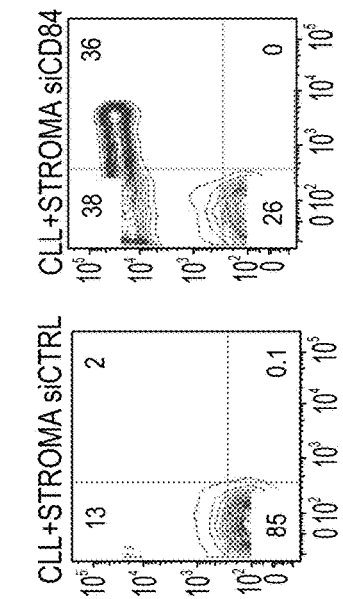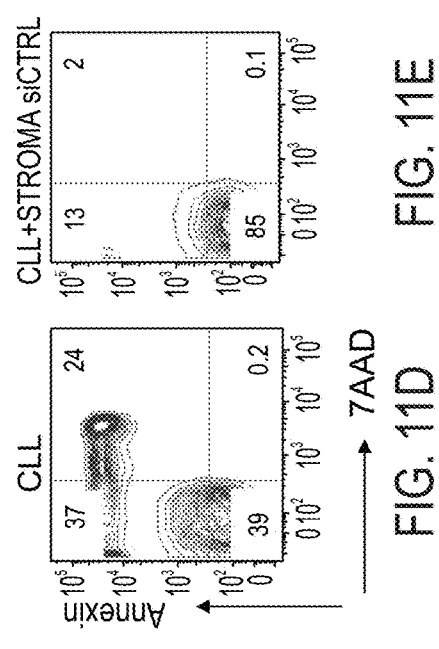

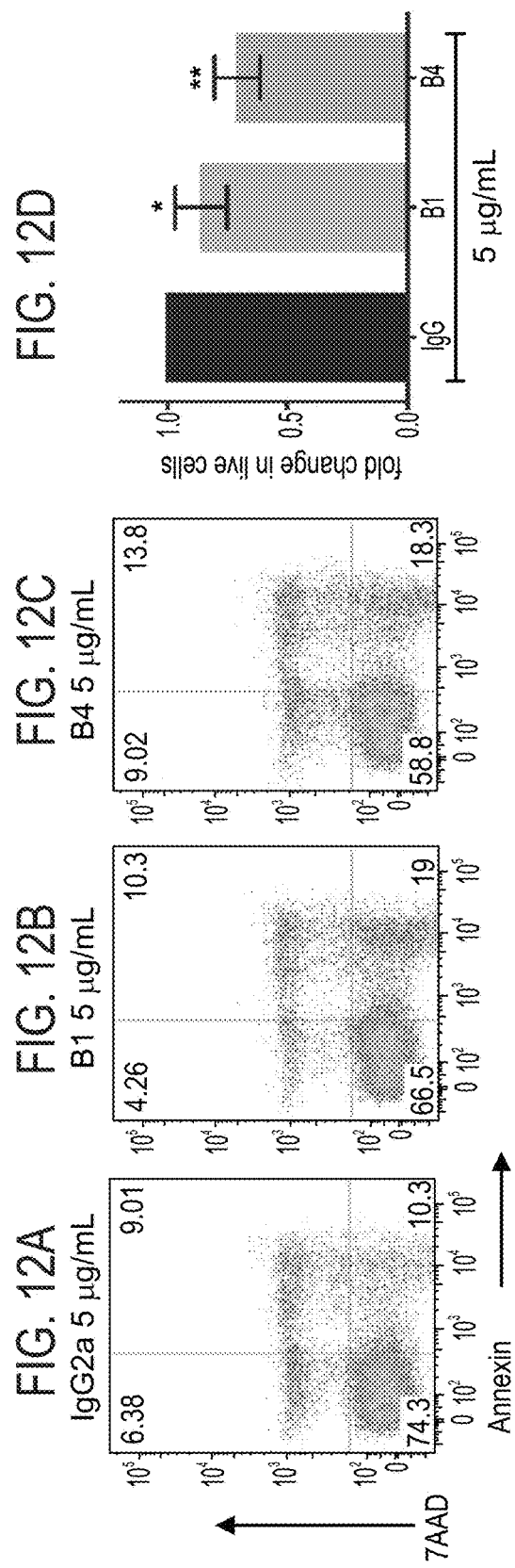

SEQUENCE LISTING

<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: B4-Heavy Chain CDR1

<400> SEQUENCE: 1

Ser Tyr Trp Met Gln
1               5

<210> SEQ ID NO 2
<211> LENGTH: 17
<212> TYPE: PRT
<213> ORGANISM: Artificial Sequence
<220> FEATURE:
<223> OTHER INFORMATION: B4-Heavy Chain CDR2

<400> SEQUENCE: 2

Ala Ile Tyr Pro Gly Asp Gly Asp Thr Arg Tyr Thr Gln Lys Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: B4-Heavy Chain CDR3

<400> SEQUENCE: 3

Leu Leu Arg Thr Tyr Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: B4-Light Chain CDR1

<400> SEQUENCE: 4

Lys Ala Ser Gln Asp Val Gly Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: B4-Light Chain CDR2

<400> SEQUENCE: 5

Trp Ala Ser Thr Arg His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: B4-Light Chain CDR3

```
<400> SEQUENCE: 6

Gln Gln Tyr Ser Ser Tyr Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: B1-Heavy Chain CDR1

<400> SEQUENCE: 7

Ser Phe Gly Met His
1               5

<210> SEQ ID NO 8
<211> LENGTH: 17
<212> TYPE: PRT
<213> ORGANISM: Artificial Sequence
<220> FEATURE:
<223> OTHER INFORMATION: B1-Heavy Chain CDR2

<400> SEQUENCE: 8

Tyr Ile Ser Ser Gly Ser Ser Thr Ile Tyr Tyr Ala Asp Thr Val Lys
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: B1-Heavy Chain CDR3

<400> SEQUENCE: 9

Trp Gly Trp Thr Gly Thr Gly Leu Asp Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: B1-Light Chain CDR1

<400> SEQUENCE: 10

Ser Val Ser Ser Ser Ile Ser Ser Ser Asn Leu His
1               5                   10

<210> SEQ ID NO 11
<211> LENGTH: 8
<212> TYPE: PRT
<213> ORGANISM: Artificial Sequence
<220> FEATURE:
<223> OTHER INFORMATION: B1-Light Chain CDR2

<400> SEQUENCE: 11

Tyr Gly Thr Ser Asn Leu Ala Ser
1               5

<210> SEQ ID NO 12
<211> LENGTH: 10
<212> TYPE: PRT
<213> ORGANISM: Artificial Sequence
<220> FEATURE:
<223> OTHER INFORMATION: B1-Light Chain CDR3
```

<400> SEQUENCE: 12

Gln Gln Trp Ser Ser Tyr Pro Phe Thr Phe
1               5                   10

<210> SEQ ID NO 13
<211> LENGTH: 1067
<212> TYPE: DNA
<213> ORGANISM: Homo sapiens

<400> SEQUENCE: 13

```
cggctcaagt gaactgactc tgctagaaca gtgccgtgct tttccacaga aggttagacc      60
ctgaaagaga tggctcagca ccacctatgg atcttgctcc tttgcctgca aacctggccg     120
gaagcagctg gaaaagactc agaaatcttc acagtgaatg ggattctggg agagtcagtc     180
actttccctg taaatatcca agaaccacgg caagttaaaa tcattgcttg gacttctaaa     240
acatctgttg cttatgtaac accaggagac tcagaaacag cacccgtagt tactgtgacc     300
cacagaaatt attatgaacg gatacatgcc ttaggtccga actacaatct ggtcattagc     360
gatctgagga tggaagacgc aggagactac aaagcagaca taaatacaca ggctgatccc     420
tacaccacca ccaagcgcta caacctgcaa atctatcgtc ggcttgggaa accaaaaatt     480
acacagagtt taatggcatc tgtgaacagc acctgtaatg tcacactgac atgctctgta     540
gagaaagaag aaaagaatgt gacatacaat tggagtcccc tgggagaaga gggtaatgtc     600
cttcaaatct tccagactcc tgaggaccaa gagctgactt acacgtgtac agcccagaac     660
cctgtcagca caattctga ctccatctct gcccggcagc tctgtgcaga catcgcaatg     720
ggcttccgta ctcaccacac cgggttgctg agcgtgctgg ctatgttctt tctgcttgtt     780
ctcattctgt cttcagtgtt tttgttccgt tgttcaaga aagacaaga tgctgcctca     840
aagaaaacca tatacacata tatcatggct tcaaggaaca cccagccagc agagtccaga     900
atctatgatg aaatcctgca gtccaaggtg cttccctcca aggaagagcc agtgaacaca     960
gtttattccg aagtgcagtt tgctgataag atggggaaag ccagcacaca ggacagtaaa    1020
cctcctggga cttcaagcta tgaaattgtg atctaggctg ctgggct                  1067
```

<210> SEQ ID NO 14
<211> LENGTH: 328
<212> TYPE: PRT
<213> ORGANISM: Homo sapiens

<400> SEQUENCE: 14

Met Ala Gln His His Leu Trp Ile Leu Leu Cys Leu Gln Thr Trp
1               5                   10                  15

Pro Glu Ala Ala Gly Lys Asp Ser Glu Ile Phe Thr Val Asn Gly Ile
                20                  25                  30

Leu Gly Glu Ser Val Thr Phe Pro Val Asn Ile Gln Glu Pro Arg Gln
            35                  40                  45

Val Lys Ile Ile Ala Trp Thr Ser Lys Thr Ser Val Ala Tyr Val Thr
        50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
                100                 105                 110

```
Thr Gln Ala Asp Pro Tyr Thr Thr Lys Arg Tyr Asn Leu Gln Ile
            115                 120                 125

Tyr Arg Arg Leu Gly Lys Pro Lys Ile Thr Gln Ser Leu Met Ala Ser
130                 135                 140

Val Asn Ser Thr Cys Asn Val Thr Leu Thr Cys Ser Val Glu Lys Glu
145                 150                 155                 160

Glu Lys Asn Val Thr Tyr Asn Trp Ser Pro Leu Gly Glu Glu Gly Asn
                165                 170                 175

Val Leu Gln Ile Phe Gln Thr Pro Glu Asp Gln Glu Leu Thr Tyr Thr
            180                 185                 190

Cys Thr Ala Gln Asn Pro Val Ser Asn Asn Ser Asp Ser Ile Ser Ala
        195                 200                 205

Arg Gln Leu Cys Ala Asp Ile Ala Met Gly Phe Arg Thr His His Thr
210                 215                 220

Gly Leu Leu Ser Val Leu Ala Met Phe Phe Leu Val Leu Ile Leu
225                 230                 235                 240

Ser Ser Val Phe Leu Phe Arg Leu Phe Lys Arg Arg Gln Asp Ala Ala
                245                 250                 255

Ser Lys Lys Thr Ile Tyr Thr Tyr Ile Met Ala Ser Arg Asn Thr Gln
            260                 265                 270

Pro Ala Glu Ser Arg Ile Tyr Asp Glu Ile Leu Gln Ser Lys Val Leu
        275                 280                 285

Pro Ser Lys Glu Glu Pro Val Asn Thr Val Tyr Ser Glu Val Gln Phe
290                 295                 300

Ala Asp Lys Met Gly Lys Ala Ser Thr Gln Asp Ser Lys Pro Pro Gly
305                 310                 315                 320

Thr Ser Ser Tyr Glu Ile Val Ile
                325

<210> SEQ ID NO 15
<211> LENGTH: 239
<212> TYPE: PRT
<213> ORGANISM: Artificial Sequence
<220> FEATURE:
<223> OTHER INFORMATION: Extracellular portion of CD84

<400> SEQUENCE: 15

Met Ala Gln His His Leu Trp Ile Leu Leu Leu Cys Leu Gln Thr Trp
1               5                   10                  15

Pro Glu Ala Ala Gly Lys Asp Ser Glu Ile Phe Thr Val Asn Gly Ile
                20                  25                  30

Leu Gly Glu Ser Val Thr Phe Pro Val Asn Ile Gln Glu Pro Arg Gln
            35                  40                  45

Val Lys Ile Ile Ala Trp Thr Ser Lys Thr Ser Val Ala Tyr Val Thr
        50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Leu Met Ala Ser Val Asn Ser Thr
        115                 120                 125

Cys Asn Val Thr Leu Thr Cys Ser Val Glu Lys Glu Glu Lys Asn Val
130                 135                 140
```

-continued

```
Thr Tyr Asn Trp Ser Pro Leu Gly Glu Glu Gly Asn Val Leu Gln Ile
145                 150                 155                 160

Phe Gln Thr Pro Glu Asp Gln Glu Leu Thr Tyr Thr Cys Thr Ala Gln
                165                 170                 175

Asn Pro Val Ser Asn Ser Asp Ser Ile Ser Ala Arg Gln Leu Cys
            180                 185                 190

Ala Asp Ile Ala Met Gly Phe Arg Glu Phe Cys Arg Tyr Pro Ala Gln
        195                 200                 205

Trp Arg Pro Leu Glu Ser Arg Gly Pro Phe Glu Gln Lys Leu Ile Ser
    210                 215                 220

Glu Glu Asp Leu Asn Met His Thr Gly His His His His His
225                 230                 235
```

<210> SEQ ID NO 16
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 16
ggatcaggga gttggaag                                                18

<210> SEQ ID NO 17
<211> LENGTH: 16
<212> TYPE: DNA
<213> ORGANISM: Artificial Sequence
<220> FEATURE:
<223> OTHER INFORMATION: Single strand DNA oligonucleotide

<400> SEQUENCE: 17
gcactgccaa acggag                                                  16

<210> SEQ ID NO 18
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 18
cgagcagcca gtgctccaag c                                            21

<210> SEQ ID NO 19
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 19
ggctgtttgg caacaaccag tcca                                         24

<210> SEQ ID NO 20
<211> LENGTH: 16
<212> TYPE: DNA
<213> ORGANISM: Artificial Sequence
<220> FEATURE:
<223> OTHER INFORMATION: Single strand DNA oligonucleotide

<400> SEQUENCE: 20
gctaccgtcg tgactt                                                  16

<210> SEQ ID NO 21
<211> LENGTH: 16
<212> TYPE: DNA
<213> ORGANISM: Artificial Sequence
<220> FEATURE:
<223> OTHER INFORMATION: Single strand DNA oligonucleotide

<400> SEQUENCE: 21
gccggttcag gtactc                                                     16

<210> SEQ ID NO 22
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 22
ccacttcaca agtcggaggc tta                                             23

<210> SEQ ID NO 23
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 23
gcaagtgcat catcgttgtt catac                                           25

<210> SEQ ID NO 24
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 24
taccagctcc caaaatcctg                                                 20

<210> SEQ ID NO 25
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 25
tctgctaatt ccagcctcgt                                                 20

<210> SEQ ID NO 26
<211> LENGTH: 11456
<212> TYPE: DNA
<213> ORGANISM: Artificial Sequence
<220> FEATURE:
<223> OTHER INFORMATION: B4 -muIgG2a

<400> SEQUENCE: 26
attgatcata atcagccata ccacatttgt agaggtttta cttgctttaa aaaacctccc     60
acacctcccc ctgaacctga aacataaaat gaatgcaatt gttgttgtta acttgtttat    120
tgcagcttat aatggttaca ataaagcaa tagcatcaca aatttcacaa ataaagcatt     180
tttttcactg cattctagtt gtggtttgtc caaactcatc aatgtatctt atcatgtctg    240
gcggccgccg atatttgaaa atatggcata ttgaaaatgt cgccgatgtg agtttctgtg    300

```
taactgatat cgccattttt ccaaaagtga ttttgggca tacgcgatat ctggcgatag    360
cgcttatatc gtttacgggg gatggcgata gacgactttg gtgacttggg cgattctgtg    420
tgtcgcaaat atcgcagttt cgatataggt gacagacgat atgaggctat atcgccgata    480
gaggcgacat caagctggca catggccaat gcatatcgat ctatacattg aatcaatatt    540
ggccattagc catattattc attggttata tagcataaat caatattggc tattggccat    600
tgcatacgtt gtatccatat cataatatgt acatttatat ggctcatgt ccaacattac    660 cgccatgttg acattgatta ttgactagtt attaatagta atcaattacg gggtcattag    720
ttcatagccc atatatggag ttccgcgtta cataacttac ggtaaatggc ccgcctggct    780
gaccgcccaa cgaccccgc ccattgacgt caataatgac gtatgttccc atagtaacgc    840
caatagggac tttccattga cgtcaatggg tggagtattt acggtaaact gcccacttgg    900
cagtacatca agtgtatcat atgccaagta cgccccctat tgacgtcaat gacggtaaat    960
ggcccgcctg gcattatgcc cagtacatga ccttatggga ctttcctact tggcagtaca   1020
tctacgtatt agtcatcgct attaccatgg tgatgcggtt ttggcagtac atcaatgggc   1080
gtggatagcg gtttgactca cggggatttc caagtctcca ccccattgac gtcaatggga   1140
gtttgttttg gcaccaaaat caacgggact ttccaaaatg tcgtaacaac tccgccccat   1200
tgacgcaaat gggcggtagg cgtgtacggt gggaggtcta taagcaga gctcgtttag    1260 tgaaccgtca gatcgcctgg agacgccatc cacgctgttt tgacctccat agaagacacc   1320
gggaccgatc cagcctccgc ggccgggaac ggtgcattgg aacgcggatt ccccgtgcca   1380
agagtgacgt aagtaccgcc tatagagtct ataggcccac ccccttggct cttatgcat    1440 gctatactgt ttttggcttg ggtctatac accccgctt cctcatgtta taggtgatgg    1500
tatagcttag cctataggtg tgggttattg accattattg accactcccc tattggtgac   1560
gatactttcc attactaatc cataacatgg ctctttgcca caactctctt tattggctat   1620
atgccaatac actgtccttc agagactgac acggactctg tatttttaca ggatggggtc   1680
tcatttatta tttacaaatt cacatataca acaccaccgt ccccagtgcc cgcagttttt   1740
attaaacata acgtgggatc tccacgcgaa tctcgggtac gtgttccgga catgggctct   1800
tctccggtag cggcggagct tctacatccg agccctgctc ccatgcctcc agcgactcat   1860
ggtcgctcgg cagctccttg ctcctaacag tggaggccag acttaggcac agcacgatgc   1920
ccaccaccac cagtgtgccg cacaaggccg tggcggtagg gtatgtgtct gaaaatgagc   1980
tcggggagcg gcttgcacc gctgacgcat ttggaagact taaggcagcg gcagaagaag   2040
atgcaggcag ctgagttgtt gtgttctgat aagagtcaga ggtaactccc gttgcggtgc   2100
tgttaacggt ggagggcagt gtagtctgag cagtactcgt tgctgccgcg cgcgccacca   2160
gacataatag ctgacagact aacagactgt ccttccat gggtctttc tgcagtcacc   2220 gtccttgaca cgaagcttgc cgccaccatg ggatggagct gtatcatcct cttcttggta   2280
gcaacagcta caggtgaggt gaagctggtg gagtctgggg ctgagctggc aagacctggg   2340
gcttcagtga agttgtcctg caaggcttct ggctacacct ttactagcta ctggatgcag   2400
tgggtaaaac agaggcctgg acagggtctg aatggattg ggctattta tcctggagat   2460 ggtgatacta ggtacactca gaagttcaag gcaaggcca cattgactgc agataaatcc   2520
tccagcacag cctacatgca actcagcagc ttggcatctg aggactctgc ggtctattac   2580
tgtgcaagat tactacgtac ctactggtac ttcgatgtct ggggcgcagg gaccacggtc   2640
accgtctcct cattcgaagc caaaacaaca gccccatcgg tctatccact ggccctgtg    2700
```

-continued

```
tgtggagata caactggctc ctcggtgact ctaggatgcc tggtcaaggg ttatttccct    2760
gagccagtga ccttgacctg gaactctgga tccctgtcca gtggtgtgca cccttccca    2820
gctgtcctgc agtctgacct ctacaccctc agcagctcag tgactgtaac ctcgagcacc    2880
tggcccagcc agtccatcac ctgcaatgtg cccacccgg caagcagcac caaggtggac    2940
aagaaaattg agcccagagg gcccacaatc aagccctgtc ctccatgcaa atgcccagca    3000
cctaacctct tgggtggacc atccgtcttc atcttccctc caaagatcaa ggatgtactc    3060
atgatctccc tgagccccat agtcacatgt gtggtggtgg atgtgagcga ggatgaccca    3120
gatgtccaga tcagctggtt tgtgaacaac gtggaagtac acacagctca gacacaaacc    3180
catagagagg attacaacag tactctccgg gtggtcagtg ccctccccat ccagcaccag    3240
gactggatga gtggcaagga gttcaaatgc aaggtcaaca caaagaccct ccagcgccc    3300
atcgagagaa ccatctcaaa acccaagggg tcagtaagag ctccacaggt atatgtcttg    3360
cctccaccag aagaagagat gactaagaaa caggtcactc tgacctgcat ggtcacagac    3420
ttcatgcctg aagacattta cgtggagtgg accaacaacg gaaaacaga gctaaactac    3480
aagaacactg aaccagtcct ggactctgat ggttcttact tcatgtacag caagctgaga    3540
gtggaaaaga gaactgggt ggaaagaaat agctactcct gttcagtggt ccacgagggg    3600
ctgcacaatc accacacgac taagagcttc tcccggactc cgggtaaatg ataagaattc    3660
attgatcata atcagccata ccacatttgt agaggtttta cttgctttaa aaacctcccc    3720
acacctcccc ctgaacctga acataaaat gaatgcaatt gttgttgtta acttgtttat    3780
tgcagcttat aatggttaca aataaagcaa tagcatcaca aatttcacaa ataaagcatt    3840
tttttcactg cattctagtt gtggtttgtc caaactcatc aatgtatctt atcatgtctg    3900
gatcctctac gccggacgca tcgtggccgg catcaccggc gccacaggtg cggttgctgg    3960
cgcctatatc gccgacatca ccgatgggga agatcgggct cgccacttcg ggctcatgag    4020
cgcttgtttc ggcgtgggta tggtggcagg ccccgtggcc gggggactgt tgggcgccat    4080
ctccttgcat gcaccattcc ttgcggcggc ggtgctcaac ggcctcaacc tactactggg    4140
ctgcttccta atgcaggagt cgcataaggg agagcgtcga cctcgggccg cgttgctggc    4200
gttttttccat aggctccgcc ccctgacga gcatcacaaa aatcgacgct caagtcagag    4260
gtggcgaaac ccgacaggac tataaagata ccaggcgttt ccccctggaa gctccctcgt    4320
gcgctctcct gttccgaccc tgccgcttac cggatacctg tccgcctttc tcccttcggg    4380
aagcgtggcg ctttctcata gctcacgctg taggtatctc agttcggtgt aggtcgttcg    4440
ctccaagctg ggctgtgtgc acgaaccccc cgttcagccc gaccgctgcg ccttatccgg    4500
taactatcgt cttgagtcca acccggtaag acacgactta tcgccactgg cagcagccac    4560
tggtaacagg attagcagag cgaggtatgt aggcggtgct acagagttct tgaagtggtg    4620
gcctaactac ggctacacta agaacagt atttggtatc tgcgctctgc tgaagccagt    4680
taccttcgga aaaagagttg gtagctcttg atccggcaaa caaaccaccg ctggtagcgg    4740
tggtttttt gtttgcaagc agcagattac gcgcagaaaa aaaggatctc aagaagatcc    4800
tttgatcttt tctacggggt ctgacgctca gtggaacgaa aactcacgtt aagggatttt    4860
ggtcatgaga ttatcaaaaa ggatcttcac ctagatcctt ttaaattaaa aatgaagttt    4920
taaatcaatc taaagtatat atgagtaaac ttggtctgac agttaccaat gcttaatcag    4980
tgaggcacct atctcagcga tctgtctatt tcgttcatcc atagttgcct gactccccgt    5040
cgtgtagata actacgatac gggagggctt accatctggc cccagtgctg caatgatacc    5100
```

```
gcgagaccca cgctcaccgg ctccagattt atcagcaata aaccagccag ccggaagggc    5160
cgagcgcaga agtggtcctg caactttatc cgcctccatc cagtctatta attgttgccg    5220
ggaagctaga gtaagtagtt cgccagttaa tagtttgcgc aacgttgttg ccattgctac    5280
aggcatcgtg gtgtcacgct cgtcgtttgg tatggcttca ttcagctccg gttcccaacg    5340
atcaaggcga gttacatgat cccccatgtt gtgcaaaaaa gcggttagct ccttcggtcc    5400
tccgatcgtt gtcagaagta agttggccgc agtgttatca ctcatggtta tggcagcact    5460
gcataattct cttactgtca tgccatccgt aagatgcttt tctgtgactg gtgagtactc    5520
aaccaagtca ttctgagaat agtgtatgcg gcgaccgagt tgctcttgcc cggcgtcaat    5580
acgggataat accgcgccac atagcagaac tttaaaagtg ctcatcattg gaaaacgttc    5640
ttcggggcga aaactctcaa ggatcttacc gctgttgaga tccagttcga tgtaacccac    5700
tcgtgcaccc aactgatctt cagcatcttt tactttcacc agcgtttctg gtgtgagcaaa   5760 aacaggaagg caaaatgccg caaaaaaggg aataagggcg acacggaaat gttgaatact    5820
catactcttc ctttttcaat attattgaag catttatcag ggttattgtc tcatgagcgg    5880
atacatattt gaatgtattt agaaaaataa acaaataggg gttccgcgca catttccccg    5940
aaaagtgcca cctgacgtct aagaaaccat tattatcatg acattaacct ataaaaatag    6000
gcgtatcacg aggccctgat ggctctttgc ggcacccatc gttcgtaatg ttccgtggca    6060
ccgaggacaa ccctcaagag aaaatgtaat cacactggct caccttcggg tgggcctttc    6120
tgcgtttata aggagacact ttatgtttaa gaaggttggt aaattccttg cggctttggc    6180
agccaagcta gatccggctg tggaatgtgt gtcagttagg gtgtggaaag tccccaggct    6240
ccccagcagg cagaagtatg caaagcatgc atctcaatta gtcagcaacc aggtgtggaa    6300 agtcccagg ctccccagca ggcagaagta tgcaaagcat gcatctcaat tagtcagcaa    6360
ccatagtccc gcccctaact ccgcccatcc cgccctaac tccgccagt tccgccatt      6420 ctccgcccca tggctgacta atttttttta tttatgcaga ggccgaggcc gcctcggcct    6480
ctgagctatt ccagaagtag tgaggaggct ttttggagg cctaggcttt tgcaaaaagc     6540
tagcttgggg ccaccgctca gagcaccttc caccatggcc acctcagcaa gttcccactt    6600
gaacaaaaac atcaagcaaa tgtacttgtg cctgccccag ggtgagaaag tccaagccat    6660
gtatatctgg gttgatggta ctggagaagg actgcgctgc aaaacccgca ccctggactg    6720
tgagcccaag tgtgtagaag agttacctga gtggaatttt gatggctcta gtacctttca    6780
gtctgagggc tccaacagtg acatgtatct cagccctgtt gccatgtttc gggaccct     6840 ccgcagagat cccaacaagc tggtgttctg tgaagttttc aagtacaacc ggaagcctgc    6900
agagaccaat ttaaggcact cgtgtaaacg gataatggac atggtgagca accagcaccc    6960
ctggtttgga atgaacagg agtatactct gatgggaaca gatgggcacc cttttggttg     7020
gccttccaat ggctttcctg gccccaagg tccgtattac tgtggtgtgg gcgcagacaa     7080
agcctatggc agggatatcg tggaggctca ctaccgcgcc tgcttgtatg ctgggtcaa    7140 gattacagga acaaatgctg aggtcatgcc tgcccagtgg gagttccaaa taggaccctg    7200
tgaaggaatc cgcatgggag atcatctctg ggtggcccgt ttcatcttgc atcgagtatg    7260
tgaagacttt ggggtaatag caacctttga ccccaagccc attcctggga actggaatgg    7320
tgcaggctgc cataccaact ttagcaccaa ggccatgcgg gaggagaatg gtctgaagca    7380
catcgaggag gccatcgaga aactaagcaa gcggcaccgg taccacattc gagcctacga    7440
tcccaagggg ggcctggaca atgcccgtcg tctgactggg ttccacgaaa cgtccaacat    7500
```

```
caacgacttt tctgctggtg tcgccaatcg cagtgccagc atccgcattc cccggactgt    7560
cggccaggag aagaaaggtt actttgaaga ccgccgcccc tctgccaatt gtgacccctt    7620
tgcagtgaca gaagccatcg tccgcacatg ccttctcaat gagactggcg acgagccctt    7680
ccaatacaaa aactaattag actttgagtg atcttgagcc tttcctagtt catcccaccc    7740
cgccccagag agatctttgt gaaggaacct tacttctgtg gtgtgacata attggacaaa    7800
ctacctacag agatttaaag ctctaaggta aatataaaat ttttaagtgt ataatgtgtt    7860
aaactactga ttctaattgt ttgtgtattt tagattccaa cctatggaac tgatgaatgg    7920
gagcagtggt ggaatgcctt taatgaggaa aacctgtttt gctcagaaga aatgccatct    7980
agtgatgatg aggctactgc tgactctcaa cattctactc ctccaaaaaa gaagagaaag    8040
gtagaagacc ccaaggactt tccttcagaa ttgctaagtt ttttgagtca tgctgtgttt    8100
agtaatagaa ctcttgcttg ctttgctatt tacaccacaa aggaaaaagc tgcactgcta    8160
tacaagaaaa ttatgaaaaa atattctgta acctttataa gtaggcataa cagttataat    8220
cataacatac tgttttttct tactccacac aggcatagag tgtctgctat taataactat    8280
gctcaaaaat tgtgtacctt tagcttttta atttgtaaag gggttaataa ggaatatttg    8340
atgtatagtg ccttgactag agatcataat cagccatacc acatttgtag aggttttact    8400
tgctttaaaa aacctcccac acctcccccct gaacctgaaa cataaaatga atgcaattgt    8460
tgttgttaac ttgtttattg cagcttataa tggttacaaa taaagcaata gcatcacaaa    8520
tttcacaaat aaagcatttt tttcactgca ttctagttgt ggtttgtcca aactcatcaa    8580
tgtatcttat catgtctgga tctagcttcg tgtcaaggac ggtgactgca gtgaataata    8640
aaatgtgtgt ttgtccgaaa tacgcgtttt gagatttctg tcgccgacta aattcatgtc    8700
gcgcgatagt ggtgtttatc gccgatagag atggcgatat tggaaaaatc gatatttgaa    8760
aatatggcat attgaaaatg tcgccgatgt gagtttctgt gtaactgata tcgccatttt    8820
tccaaaagtg atttttgggc atacgcgata tctggcgata gcgcttatat cgtttacggg    8880
ggatggcgat agacgacttt ggtgacttgg gcgattctgt gtgtcgcaaa tatcgcagtt    8940
tcgatatagg tgacagacga tatgaggcta tatcgccgat agaggcgaca tcaagctggc    9000
acatggccaa tgcatatcga tctatacatt gaatcaatat tggccattag ccatattatt    9060
cattggttat atagcataaa tcaatattgg ctattggcca ttgcatacgt tgtatccata    9120
tcataatatg tacatttata ttggctcatg tccaacatta ccgccatgtt gacattgatt    9180
attgactagt tattaatagt aatcaattac ggggtcatta gttcatagcc catatatgga    9240
gttccgcgtt acataactta cggtaaatgg cccgcctggc tgaccgccca acgacccccg    9300
cccattgacg tcaataatga cgtatgttcc catagtaacg ccaatagggg ctttccattg    9360
acgtcaatgg gtggagtatt tacggtaaac tgcccacttg gcagtacatc aagtgtatca    9420
tatgccaagt acgccccta ttgacgtcaa tgacggtaaa tggcccgcct ggcattatgc    9480
ccagtacatg accttatggg actttcctac ttggcagtac atctacgtat tagtcatcgc    9540
tattaccatg gtgatgcggt tttggcagta catcaatggg cgtggatagc ggtttgactc    9600
acggggattt ccaagtctcc accccattga cgtcaatggg agtttgtttt ggcaccaaaa    9660
tcaacgggac tttccaaaat gtcgtaacaa ctccgcccca ttgacgcaaa tgggcggtag    9720
gcgtgtacgg tgggaggtct atataagcag agctcgttta gtgaaccgtc agatcgcctg    9780
gagacgccat ccacgctgtt ttgacctcca tagaagacac cgggaccgat ccagcctccg    9840
cggccgggaa cggtgcattg gaacgcggat tccccgtgcc aagagtgacg taagtaccgc    9900
```

```
ctatagagtc tataggccca cccccttggc ttcttatgca tgctatactg ttttttggctt      9960 ggggtctata cacccccgct tcctcatgtt ataggtgatg gtatagctta gcctataggt     10020
gtgggttatt gaccattatt gaccactccc ctattggtga cgatactttc cattactaat     10080
ccataacatg gctcttttgcc acaactctct ttattggcta tatgccaata cactgtcctt     10140
cagagactga cacggactct gtattttttac aggatggggt ctcatttatt atttacaaat    10200
tcacatatac aacaccaccg tccccagtgc ccgcagtttt tattaaacat aacgtgggat     10260
ctccacgcga atctcgggta cgtgttccgg acatgggctc ttctccggta gcggcggagc    10320
ttctacatcc gagccctgct cccatgcctc cagcgactca tggtcgctcg gcagctcctt    10380
gctcctaaca gtggaggcca gacttaggca cagcacgatg cccaccacca ccagtgtgcc    10440
gcacaaggcc gtggcggtag gtatgtgtc tgaaaatgag ctcggggagc gggcttgcac     10500
cgctgacgca tttggaagac ttaaggcagc ggcagaagaa gatgcaggca gctgagttgt    10560
tgtgttctga taagagtcag aggtaactcc cgttgcggtg ctgttaacgg tggagggcag    10620
tgtagtctga gcagtactcg ttgctgccgc gcgcgccacc agacataata gctgacagac    10680
taacagactg ttccttttcca tgggtctttt ctgcagtcac cgtccttgac acgaagcttg    10740
ccgccaccat gggatggagc tgtatcatcc tcttcttggt agcaacagct acaggtgaca    10800
ttgtgctgac ccagtctcac aaattcatgt ccacatcagt aggagacagg gtcagcatca    10860
cctgcaaggc cagtcaggat gtgggtactg ctgtagcctg gtatcaacag aaaccagggc    10920
aatctcctaa actactgatt tactgggcat ccacccggca cactggagtc cctgatcgct    10980
tcacaggcag tggatctggg acagatttca ctctcaccat tagcaatgtg cagtctgaag    11040
acttggcaga ttatttctgt cagcaatata gcagctatcc gtacacgttc ggaggggga    11100 ccaagctgga gctgaaacgg cgtacgcgtg ctgatgctgc accaactgta tccatcttcc    11160
caccatccag tgagcagtta acatctggag gtgcctcagt cgtgtgcttc ttgaacaact    11220
tctaccccaa agacatcaat gtcaagtgga agattgatgg cagtgaacga caaaatggcg    11280
tcctgaacag ttggactgat caggacagca agacagcac ctacagcatg agcagcaccc     11340
tcacgttgac caaggacgag tatgaacgac ataacagcta tacctgtgag gccactcaca    11400
agacatcaac ttcacccatt gtcaagagct tcaacaggaa tgagtgttaa gaattc         11456
```

<210> SEQ ID NO 27
<211> LENGTH: 11438
<212> TYPE: DNA
<213> ORGANISM: Artificial Sequence
<220> FEATURE:
<223> OTHER INFORMATION: B1-mIgG1 sequence

<400> SEQUENCE: 27

```
attgatcata atcagccata ccacatttgt agaggtttta cttgctttaa aaaacctccc      60
acacctcccc ctgaacctga acataaaat gaatgcaatt gttgttgtta acttgtttat       120
tgcagcttat aatggttaca aataaagcaa tagcatcaca aatttcacaa ataaagcatt      180
tttttcactg cattctagtt gtggtttgtc caaactcatc aatgtatctt atcatgtctg      240
gcggccgccg atatttgaaa atatggcata ttgaaaatgt cgccgatgtg agtttctgtg      300
taactgatat cgccattttt ccaaaagtga ttttgggca tacgcgatat ctggcgatag      360
cgcttatatc gtttacgggg gatggcgata cgacttttg gtgacttggg cgattctgtg      420
tgtcgcaaat atcgcagttt cgatataggt gacagacga atgaggctat atcgccgata     480
gaggcgacat caagctggca catggccaat gcatatcgat ctatacattg aatcaatatt     540
```

```
ggccattagc catattattc attggttata tagcataaat caatattggc tattggccat      600
tgcatacgtt gtatccatat cataatatgt acatttatat tggctcatgt ccaacattac      660
cgccatgttg acattgatta ttgactagtt attaatagta atcaattacg gggtcattag      720
ttcatagccc atatatggag ttccgcgtta cataacttac ggtaaatggc ccgcctggct      780
gaccgcccaa cgaccccgc ccattgacgt caataatgac gtatgttccc atagtaacgc       840
caatagggac tttccattga cgtcaatggg tggagtattt acggtaaact gcccacttgg      900
cagtacatca agtgtatcat atgccaagta cgccccctat tgacgtcaat gacggtaaat      960
ggcccgcctg gcattatgcc cagtacatga ccttatggga ctttcctact tggcagtaca     1020
tctacgtatt agtcatcgct attaccatgg tgatgcggtt ttggcagtac atcaatgggc     1080
gtggatagcg gtttgactca cggggatttc caagtctcca ccccattgac gtcaatggga     1140
gtttgttttg gcaccaaaat caacgggact ttccaaaatg tcgtaacaac tccgccccat     1200
tgacgcaaat gggcggtagg cgtgtacggt gggaggtcta tataagcaga gctcgtttag     1260
tgaaccgtca gatcgcctgg agacgccatc cacgctgttt tgacctccat agaagacacc     1320
gggaccgatc cagcctccgc ggccgggaac ggtgcattgg aacgcggatt ccccgtgcca     1380
agagtgacgt aagtaccgcc tatagagtct ataggcccac cccttggct tcttatgcat      1440 gctatactgt ttttggcttg ggtctatac accccgctt cctcatgtta taggtgatgg        1500
tatagcttag cctataggtg tgggttattg accattattg accactcccc tattggtgac     1560
gatactttcc attactaatc cataacatgg ctctttgcca caactctctt tattggctat     1620
atgccaatac actgtccttc agagactgac acggactctg tatttttaca ggatggggtc     1680
tcatttatta tttacaaatt cacatataca acaccaccgt ccccagtgcc cgcagttttt     1740
attaaacata acgtgggatc tccacgcgaa tctcgggtac gtgttccgga catgggctct     1800
tctccggtag cggcggagct tctacatccg agccctgctc ccatgcctcc agcgactcat     1860
ggtcgctcgg cagctccttg ctcctaacag tggaggccag acttaggcac agcacgatgc     1920
ccaccaccac cagtgtgccg cacaaggccg tggcggtagg gtatgtgtct gaaaatgagc     1980
tcggggagcg ggcttgcacc gctgacgcat ttggaagact taaggcagcg gcagaagaag     2040
atgcaggcag ctgagttgtt gtgttctgat aagagtcaga ggtaactccc gttgcggtgc     2100
tgttaacggt ggagggcagt gtagtctgag cagtactcgt tgctgccgcg cgcgccacca     2160
gacataatag ctgacagact aacagactgt tcctttccat gggtcttttc tgcagtcacc     2220
gtccttgaca cgaagcttgc cgccaccatg ggatggagct gtatcatcct cttcttggta     2280
gcaacagcta caggtgaggt gaagctggtg gaatctgggg gaggcttagt gcagcctgga     2340
gggtcccgga aactctcctg tgcagcctct ggattcactt tcagtagctt tggaatgcac     2400
tgggttcgtc aggctccaga aaggggctg gagtgggtcg catacattag tagtggcagt      2460
agtaccatct actatgcaga cacagtgaag ggccgattca ccatctccag agacaatccc     2520
aagaacaccc tgttcctgca aatgaccagt ctaaggtctg aggacacggc catgtattac     2580
tgtgcaagat gggggtggac tgggacagga cttgactact ggggccaagg caccactctc     2640
acagtctcct cattcgaagc caaaacgaca ccccatctg tctatccact ggcccctgga      2700
tctgctgccc aaactaactc catggtgacc ctgggatgcc tggtcaaggg ctatttccct     2760
gagccagtga cagtgacctg gaactctgga tccctgtcca gcggtgtgca caccttccca     2820
gctgtcctgc agtctgacct ctacactctg agcagctcag tgactgtccc ctccagcacc     2880
tggcccagcg agaccgtcac ctgcaacgtt gcccaccccg gccagcagca caaggtggac     2940
```

```
aagaaaattg tgcccaggga ttgtggttgt aagccttgca tatgtacagt cccagaagta   3000
tcatctgtct tcatcttccc cccaaagccc aaggatgtgc tcaccattac tctgactcct   3060
aaggtcacgt gtgttgtggt agacatcagc aaggatgatc ccgaggtcca gttcagctgg   3120
tttgtagatg atgtggaggt gcacacagct cagacgcaac cccgggagga gcagttcaac   3180
agcactttcc gctcagtcag tgaacttccc atcatgcacc aggactggct caatggcaag   3240
gagttcaaat gcagggtcaa cagtgcagct ttccctgccc ccatcgagaa aaccatctcc   3300
aaaaccaaag gcagaccgaa ggctccacag gtgtacacca ttccacctcc caaggagcag   3360
atggccaagg ataaagtcag tctgacctgc atgataacag acttcttccc tgaagacatt   3420
actgtggagt ggcagtggaa tgggcagcca gcggagaact acaagaacac tcagcccatc   3480
atggacacag atggctctta cttcgtctac agcaagctca atgtgcagaa gagcaactgg   3540
gaggcaggaa atactttcac ctgctctgtg ttacatgagg gcctgcacaa ccaccatact   3600
gagaagagcc tctcccactc tcctggtaaa tgagaattca ttgatcataa tcagccatac   3660
cacatttgta gaggttttac ttgctttaaa aaacctccca cacctccccc tgaacctgaa   3720
acataaaatg aatgcaattg ttgttgttaa cttgtttatt gcagcttata atggttacaa   3780
ataaagcaat agcatcacaa atttcacaaa taaagcattt ttttcactgc attctagttg   3840
tggtttgtcc aaactcatca atgtatctta tcatgtctgg atcctctacg ccggacgcat   3900
cgtggccggc atcaccggcg ccacaggtgc ggttgctggc gcctatatcg ccgacatcac   3960
cgatggggaa gatcgggctc gccacttcgg gctcatgagc gcttgtttcg gcgtgggtat   4020
ggtggcaggc cccgtggccg ggggactgtt gggcgccatc tccttgcatg caccattcct   4080
tgcggcggcg gtgctcaacg gcctcaacct actactgggc tgcttcctaa tgcaggagtc   4140
gcataaggga gagcgtcgac ctcgggccgc gttgctggcg ttttttccata ggctccgccc   4200 ccctgacgag catcacaaaa atcgacgctc aagtcagagg tggcgaaacc cgacaggact   4260
ataaagatac caggcgtttc cccctggaag ctccctcgtg cgctctcctg ttccgaccct   4320
gccgcttacc ggatacctgt ccgcctttct cccttcggga agcgtggcgc tttctcatag   4380
ctcacgctgt aggtatctca gttcggtgta ggtcgttcgc tccaagctgg gctgtgtgca   4440 cgaaccccc gttcagcccg accgctgcgc cttatccggt aactatcgtc ttgagtccaa   4500
cccggtaaga cacgacttat cgccactggc agcagccact ggtaacagga ttagcagagc   4560
gaggtatgta ggcggtgcta cagagttctt gaagtggtgg cctaactacg gctacactag   4620
aagaacagta tttggtatct gcgctctgct gaagccagtt accttcggaa aaagagttgg   4680
tagctcttga tccggcaaac aaaccaccgc tggtagcggt ggtttttttg tttgcaagca   4740
gcagattacg cgcagaaaaa aaggatctca agaagatcct ttgatctttt ctacggggtc   4800
tgacgctcag tggaacgaaa actcacgtta agggattttg gtcatgagat tatcaaaaag   4860
gatcttcacc tagatccttt taaattaaaa atgaagtttt aaatcaatct aaagtatata   4920
tgagtaaact tggtctgaca gttaccaatg cttaatcagt gaggcaccta tctcagcgat   4980
ctgtctattt cgttcatcca tagttgcctg actccccgtc gtgtagataa ctacgatacg   5040
ggagggctta ccatctggcc ccagtgctgc aatgataccg cgagacccac gctcaccggc   5100
tccagattta tcagcaataa accagccagc cggaagggcc gagcgcagaa gtggtcctgc   5160
aactttatcc gcctccatcc agtctattaa ttgttgccgg gaagctagag taagtagttc   5220
gccagttaat agtttgcgca acgttgttgc cattgctaca ggcatcgtgg tgtcacgctc   5280
gtcgtttggt atggcttcat tcagctccgg ttcccaacga tcaaggcgag ttacatgatc   5340
```

```
ccccatgttg tgcaaaaaag cggttagctc cttcggtcct ccgatcgttg tcagaagtaa    5400
gttggccgca gtgttatcac tcatggttat ggcagcactg cataattctc ttactgtcat    5460
gccatccgta agatgctttt ctgtgactgg tgagtactca accaagtcat tctgagaata    5520
gtgtatgcgg cgaccgagtt gctcttgccc ggcgtcaata cgggataata ccgcgccaca    5580
tagcagaact ttaaaagtgc tcatcattgg aaaacgttct cggggcgaaa actctcaag    5640
gatcttaccg ctgttgagat ccagttcgat gtaaccact cgtgcaccca actgatcttc    5700
agcatctttt actttcacca gcgtttctgg gtgagcaaaa acaggaaggc aaaatgccgc    5760
aaaaaaggga ataagggcga cacggaaatg ttgaatactc atactcttcc tttttcaata    5820
ttattgaagc atttatcagg gttattgtct catgagcgga tacatatttg aatgtattta    5880
gaaaaataaa caatagggg ttccgcgcac atttccccga aaagtgccac ctgacgtcta    5940
agaaaccatt attatcatga cattaaccta taaaaatagg cgtatcacga ggccctgatg    6000
gctctttgcg gcacccatcg ttcgtaatgt tccgtggcac cgaggacaac cctcaagaga    6060
aaatgtaatc acactggctc accttcgggt gggcctttct gcgtttataa ggagacactt    6120
tatgtttaag aaggttggta aattccttgc ggctttggca gccaagctag atccggctgt    6180
ggaatgtgtg tcagttaggg tgtggaaagt ccccaggctc cccagcaggc agaagtatgc    6240
aaagcatgca tctcaattag tcagcaacca ggtgtggaaa gtccccaggc tccccagcag    6300
gcagaagtat gcaaagcatg catctcaatt agtcagcaac catagtcccg cccctaactc    6360
cgcccatccc gcccctaact ccgcccagtt ccgcccattc tccgcccat ggctgactaa    6420
ttttttttat ttatgcagag gccgaggccg cctcggcctc tgagctattc cagaagtagt    6480
gaggaggctt ttttggaggc ctaggctttt gcaaaaagct agcttggggc caccgctcag    6540
agcaccttcc accatggcca cctcagcaag ttcccacttg aacaaaaaca tcaagcaaat    6600
gtacttgtgc ctgccccagg gtgagaaagt ccaagccatg tatatctggg ttgatggtac    6660
tggagaagga ctgcgctgca aaacccgcac cctggactgt gagcccaagt gtgtagaaga    6720
gttacctgag tggaatttg atggctctag tacctttcag tctgagggct ccaacagtga    6780
catgtatctc agccctgttg ccatgttccg ggaccccttc cgcagagatc caacaagct    6840
ggtgttctgt gaagttttca agtacaaccg gaagcctgca gagaccaatt taaggcactc    6900
gtgtaaacgg ataatggaca tggtgagcaa ccagcacccc tggtttggaa tggaacagga    6960
gtatactctg atgggaacag atgggcaccc ttttggttgg ccttccaatg gctttcctgg    7020
gccccaaggt ccgtattact gtggtgtggg cgcagacaaa gcctatggca gggatatcgt    7080
ggaggctcac taccgcgcct gcttgtatgc tggggtcaag attacaggaa caaatgctga    7140
ggtcatgcct gccagtgggg agttccaaat aggaccctgt gaaggaatcc gcatgggaga    7200
tcatctctgg gtggcccgtt tcatcttgca tcgagtatgt gaagactttg gggtaatagc    7260
aacctttgac cccaagccca ttcctgggaa ctggaatggt gcaggctgcc ataccaactt    7320
tagcaccaag gccatgcggg aggagaatgg tctgaagcac atcgaggagg ccatcgagaa    7380
actaagcaag cggcaccggt accacattcg agcctacgat cccaaggggg gcctggacaa    7440
tgcccgtcgt ctgactgggt tccacgaaac gtccaacatc aacgactttt ctgctggtgt    7500
cgccaatcgc agtgccagca tccgcattcc ccggactgtc ggccaggaga agaaggtta    7560
ctttgaagac cgccgcccct ctgccaattg tgaccccttt gcagtgacag aagccatcgt    7620
ccgcacatgc cttctcaatg agactggcga cgagcccttc caatacaaaa actaattaga    7680
ctttgagtga tcttgagcct ttcctagttc atcccacccc gccccagaga gatctttgtg    7740
```

```
aaggaacctt acttctgtgg tgtgacataa ttggacaaac tacctacaga gatttaaagc   7800
tctaaggtaa atataaaatt tttaagtgta taatgtgtta aactactgat tctaattgtt   7860
tgtgtatttt agattccaac ctatggaact gatgaatggg agcagtggtg gaatgccttt   7920
aatgaggaaa acctgttttg ctcagaagaa atgccatcta gtgatgatga ggctactgct   7980
gactctcaac attctactcc tccaaaaaag aagagaaagg tagaagaccc caaggacttt   8040
ccttcagaat tgctaagttt tttgagtcat gctgtgttta gtaatagaac tcttgcttgc   8100 tttgctatt acaccacaaa ggaaaaagct gcactgctat acaagaaaat tatggaaaaa   8160
tattctgtaa cctttataag taggcataac agttataatc ataacatact gttttttctt   8220
actccacaca ggcatagagt gtctgctatt aataactatg ctcaaaaatt gtgtaccttt   8280
agctttttaa tttgtaaagg ggttaataag gaatatttga tgtatagtgc cttgactaga   8340
gatcataatc agccatacca catttgtaga ggttttactt gctttaaaaa acctcccaca   8400 cctcccctg aacctgaaac ataaaatgaa tgcaattgtt gttgttaact tgtttattgc   8460
agcttataat ggttacaaat aaagcaatag catcacaaat ttcacaaata aagcattttt   8520
ttcactgcat tctagttgtg gtttgtccaa actcatcaat gtatcttatc atgtctggat   8580
ctagcttcgt gtcaaggacg gtgactgcag tgaataataa aatgtgtgtt tgtccgaaat   8640
acgcgttttg agatttctgt cgccgactaa attcatgtcg cgcgatagtg gtgtttatcg   8700
ccgatagaga tggcgatatt ggaaaaatcg atatttgaaa atatggcata ttgaaaatgt   8760
cgccgatgtg agtttctgtg taactgatat cgccattttt ccaaaagtga ttttgggca   8820 tacgcgatat ctggcgatag cgcttatatc gtttacgggg gatggcgata gacgactttg   8880
gtgacttggg cgattctgtg tgtcgcaaat atcgcagttt cgatataggt gacagacgat   8940
atgaggctat atcgccgata gaggcgacat caagctggca catggccaat gcatatcgat   9000
ctatacattg aatcaatatt ggccattagc catattattc attggttata tagcataaat   9060
caatattggc tattgccat tgcatacgtt gtatccatat cataatatgt acatttatat   9120
tggctcatgt ccaacattac cgccatgttg acattgatta ttgactagtt attaatagta   9180
atcaattacg gggtcattag ttcatagccc atatatggag ttccgcgtta cataacttac   9240
ggtaaatggc ccgcctggct gaccgcccaa cgacccccgc ccattgacgt caataatgac   9300
gtatgttccc atagtaacgc caatagggac tttccattga cgtcaatggg tggagtattt   9360
acggtaaact gcccacttgg cagtacatca agtgtatcat atgccaagta cgccccctat   9420
tgacgtcaat gacggtaaat ggcccgcctg gcattatgcc cagtacatga ccttatggga   9480
ctttcctact tggcagtaca tctacgtatt agtcatcgct attaccatgg tgatgcggtt   9540
ttggcagtac atcaatgggc gtggatagcg gtttgactca cggggatttc caagtctcca   9600
ccccattgac gtcaatggga gtttgttttg gcaccaaaat caacgggact ttccaaaatg   9660
tcgtaacaac tccgccccat tgacgcaaat gggcggtagg cgtgtacggt gggaggtcta   9720
tataagcaga gctcgtttag tgaaccgtca gatcgcctgg agacgccatc cacgctgttt   9780
tgacctccat agaagacacc gggaccgatc cagcctccgc ggccgggaac ggtgcattgg   9840
aacgcggatt cccgtgcca agagtgacgt aagtaccgcc tatagagtct ataggcccac   9900 cccccttggct tcttatgcat gctatactgt ttttggcttg gggtctatac accccgcttt   9960
cctcatgtta taggtgatgg tatagcttag cctataggtg tgggttattg accattattg   10020
accactcccc tattggtgac gatactttcc attactaatc cataacatgg ctctttgcca   10080
caactctctt tattggctat atgccaatac actgtccttc agagactgac acggactctg   10140
```

```
tattttttaca ggatggggtc tcatttatta tttacaaatt cacatataca acaccaccgt    10200
ccccagtgcc cgcagttttt attaaacata acgtgggatc tccacgcgaa tctcgggtac    10260
gtgttccgga catgggctct tctccggtag cggcggagct tctacatccg agccctgctc    10320
ccatgcctcc agcgactcat ggtcgctcgg cagctccttg ctcctaacag tggaggccag    10380
acttaggcac agcacgatgc ccaccaccac cagtgtgccg cacaaggccg tggcggtagg    10440
gtatgtgtct gaaaatgagc tcggggagcg ggcttgcacc gctgacgcat ttggaagact    10500
taaggcagcg gcagaagaag atgcaggcag ctgagttgtt gtgttctgat aagagtcaga    10560
ggtaactccc gttgcggtgc tgttaacggt ggagggcagt gtagtctgag cagtactcgt    10620
tgctgccgcg cgcgccacca gacataatag ctgacagact aacagactgt tcctttccat    10680
gggtcttttc tgcagtcacc gtccttgaca cgaagcttgc cgccaccatg gatggagct    10740 gtatcatcct cttcttggta gcaacagcta caggtgatat tgtgctaact cagtctccag    10800
cactcatggc tgcatctcca ggggagaagg tcaccatcac ctgcagtgtc agctcaagta    10860
taagttccag caacttgcac tggtaccagc agaagtcaga aacctccccc aaaccctgga    10920
tttatggcac atccaacctg gcttctggag tccctgttcg cttcagtggc agtggatctg    10980
ggacctctta ttctctcaca atcagcagca tggaggctga agatgctgcc acttattact    11040
gtcaacagtg gagtagttac ccattcacgt tcggctcggg gaccaagctg gaaataaaac    11100
ggcgtacgcg tgctgatgct gcaccaactg tatccatctt cccaccatcc agtgagcagt    11160
taacatctgg aggtgcctca gtcgtgtgct tcttgaacaa cttctacccc aaagacatca    11220
atgtcaagtg gaagattgat ggcagtgaac gacaaaatgg cgtcctgaac agttggactg    11280
atcaggacag caaagacagc acctacagca tgagcagcac cctcacgttg accaaggacg    11340
agtatgaacg acataacagc tatacctgtg aggccactca caagacatca acttcaccca    11400
ttgtcaagag cttcaacagg aatgagtgtt aagaattc                            11438

<210> SEQ ID NO 28
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 28
ttgttccgtt tgttcaagag                                                20

<210> SEQ ID NO 29
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 29
cggaataaac tgtgttcact g                                              21
```

ANTI CD84 ANTIBODIES, COMPOSITIONS COMPRISING SAME AND USES THEREOF

RELATED APPLICATIONS

This application is a National Phase of PCT Patent Application No. PCT/IL2015/050133 having International filing date of Feb. 5, 2015, which claims the benefit of priority under 35 USC § 119(e) of U.S. Provisional Patent Application No. 61/936,361 filed on Feb. 6, 2014. The contents of the above applications are all incorporated by reference as if fully set forth herein in their entirety.

SEQUENCE LISTING STATEMENT

The ASCII file, entitled 66892SequenceListing.txt, created on Aug. 3, 2016 comprising 43,095 bytes, submitted concurrently with the filing of this application is incorporated herein by reference.

FIELD AND BACKGROUND OF THE INVENTION

The present invention, in some embodiments thereof, relates to anti CD84 antibodies, compositions comprising same and uses thereof.

In normal individuals, the pool of peripheral lymphocytes is constant in size. The control of lymphoid homeostasis is the result of a very fine balance between lymphocyte production, survival, and proliferation. Survival factors have been shown to play a critical role in maintaining lymphocyte homeostasis.

Chronic lymphocytic leukemia, the most common leukemia in the Western world, is characterized by the progressive accumulation of $CD5^+$ small mature lymphocytes, in the peripheral blood, lymphoid organs and bone marrow. The hallmark of the disease is decreased apoptosis, resulting in accumulation of these malignant cells. Despite major progress in the last few years in the understanding of the biology and pathophysiology of the disease, as well as the development of better treatment modalities, CLL remains incurable in most patients, and even control of the disease requires aggressive treatment with significant side effects. A better understanding of the cellular events involved in the pathogenesis and progression of the disease should lead to more targeted and less toxic therapies, with early treatment in patients at risk, possibly enabling cure.

CD84 is a member of the CD2 subset of the immunoglobulin superfamily of cell surface molecules. It is a single chain cell-surface protein with an extracellular portion of 199 aa, which contains four potential N-glycosylation sites. The transmembrane region consists of 25 aa, and the 83 aa cytoplasmic tail contains four tyrosines [delaFuente et al. Blood. 1997; 90:2398-2405]. The human CD84 is 57.3% identical to murine CD84. CD84 is predominantly expressed by B cells, T cells, platelets, monocytes, dendritic cells (DCs), and CD84 is also expressed early in hematopoiesis [Calpe et al. Advances in Immunology, Vol 97. 2008; 97:177-250].

The present inventors have previously shown that the expression of CD84 is significantly elevated from the early stages of the disease, and is regulated by macrophage migration inhibitory factor and its receptor, CD74. Activation of cell surface CD84 initiates a signaling cascade that enhances CLL cell survival. Both downmodulation of CD84 expression and its immune-mediated blockade induce cell death in vitro and in vivo. In addition, analysis of samples derived from an on-going clinical trial, in which human subjects were treated with humanized anti-CD74 (milatuzumab), shows a decrease in CD84 messenger RNA and protein levels in milatuzumab-treated cells. This downregulation was correlated with reduction of Bcl-2 and Mcl-1 expression. Thus, overexpression of CD84 in CLL is an important survival mechanism that appears to be an early event in the pathogenesis of the disease (Binsky-Ehrenreich et al. E. Pub. Feb. 25, 2013 Oncogene).

WO2010/035259 teaches CD84 as a regulator protein that is essential for the survival of CLL cells. Based on this finding, the inventors of WO2010/035259 have suggested the use of CD84 as a target for B-CLL treatment and as a marker for the disease.

ADDITIONAL RELATED ART

U.S. Patent Application No. 20050027114 discloses methods of treating diseases such as chronic leukemia by agonizing or antagonizing an activity of a CD84-like polypeptide.

U.S. Patent Application No. 20050025789 discloses the treatment or prophylaxis of tumors in patients, using a co-stimulatory polypeptide (e.g., CD84)-expressing tumor cell for producing a vaccine for increasing the lytic activity of NK cells.

SUMMARY OF THE INVENTION

According to an aspect of some embodiments of the present invention there is provided an isolated antibody comprising an antigen recognition domain which specifically binds CD84 and:
(i) down regulates the anti-apoptotic activity of stromal cells on chronic lymphocytic leukemia (CLL) cells; and/or
(ii) induces mobilization of CLL cells from the bone marrow.

According to an aspect of some embodiments of the present invention there is provided an isolated antibody comprising an antigen recognition domain comprising complementarity determining regions as set forth in SEQ ID NOs: 1, 2, 3, 4, 5 and 6 (B4), wherein the antibody specifically binds CD84.

According to an aspect of some embodiments of the present invention there is provided an isolated antibody comprising an antigen recognition domain comprising complementarity determining regions as set forth in SEQ ID NOs: 7, 8, 9, 10, 11 and 12 (B1), wherein the antibody specifically binds CD84.

According to some embodiments of the invention, the isolated antibody down regulates the anti-apoptotic activity of stromal cells on chronic lymphocytic leukemia (CLL) cells.

According to some embodiments of the invention, the isolated antibody inhibits the secretion of CCL3 from CLL cells.

According to some embodiments of the invention, the isolated antibody inhibits the expression of BCL-2 in CLL and stromal cells.

According to some embodiments of the invention, the isolated antibody inhibits the expression of stroma Bcl-2, thereby reducing the anti-apoptotic effect of the stroma on CLL.

According to some embodiments of the invention, the isolated antibody reduces the expression of cytokine like IL-6 and IL-8 in stromal cells that supports CLL survival.

According to some embodiments of the invention, the isolated antibody induces mobilization of CLL cells from the bone marrow.

According to some embodiments of the invention, the isolated antibody is an IgG.

According to some embodiments of the invention, the antibody is a humanized antibody or a chimeric antibody.

According to some embodiments of the invention, the antibody is a bispecific antibody.

According to an aspect of some embodiments of the present invention there is provided a pharmaceutical composition comprising the isolated antibody and a pharmaceutically acceptable carrier or diluent.

According to an aspect of some embodiments of the present invention there is provided a method of inducing apoptosis in B cells of a subject having a B cell malignancy, the method comprising administering to the subject a therapeutically effective amount of the antibody, thereby inducing apoptosis in B cells of the subject.

According to an aspect of some embodiments of the present invention there is provided a method of treating a B cell malignancy in a subject in need thereof, the method comprising administering to the subject a therapeutically effective amount of the antibody, thereby treating the B cell malignancy.

According to an aspect of some embodiments of the present invention there is provided use of the antibody in the manufacture of a medicament identified for the treatment of a B cell malignancy.

According to some embodiments of the invention, the B cell malignancy is selected from the group consisting of a lymphoma, a leukemia and a myeloma.

According to some embodiments of the invention, the B cell malignancy is selected from the group consisting of a Hodgkin's Lymphoma, a non-Hodgkin's Lymphoma, a Diffuse large B-cell lymphoma, a B-cell chronic lymphocytic leukemia (B-CLL)/chronic lymphoid leukemia (CLL), a Chronic lymphocytic leukemia/small lymphocytic lymphoma, a chronic myelocytic leukemia (CML), an Extranodal marginal zone B-cell lymphoma—mucosa-associated lymphoid tissue lymphoma, a Follicular lymphoma, a Mantle cell lymphoma, a Nodal marginal zone B-cell lymphoma, a Burkitt's lymphoma, a Hairy cell leukemia, a Primary central nervous system lymphoma, a Splenic marginal zone B-cell lymphoma, a Lymphoplasmocytic lymphoma, a Primary mediastinal B-cell lymphoma, a multiple myeloma, an acute lymphocytic leukemia (ALL), an acute lymphoblastic pre-B cell leukemia, a plasma cell leukemia, a pre-B cell leukemia, an early pre-B cell leukemia and a pre-B acute lymphoblastoid leukemia.

According to some embodiments of the invention, the B cell malignancy is a B-CLL.

According to an aspect of some embodiments of the present invention there is provided a method of diagnosing B-CLL in a subject in need thereof, the method comprising:

(a) contacting a biological sample of the subject with the antibody of any one of claims 1-12 under conditions which allow the formation of immunocomplexes between CD84 isoform C (SEQ ID NO: 14) and the antibody; and (b) determining a level of the immunocomplexes in the biological sample, wherein an increase in level of the immunocomplexes beyond a predetermined threshold with respect to a level of the immunocomplexes in a biological sample from a healthy individual is indicative of the B-CLL.

According to some embodiments of the invention, the determining is effected at the protein level.

According to some embodiments of the invention, the method further comprises corroborating the diagnosis using a diagnostic assay selected from surface marker expression distinctive of the CD84 isoform c, karyotype analysis and germline mutations.

According to some embodiments of the invention, an isolated polynucleotide comprising a nucleic acid sequence encoding the antibody.

According to some embodiments of the invention, the isolated polynucleotide is as set forth in SEQ ID NO: 26 or 27.

According to an aspect of some embodiments of the present invention there is provided a method of identifying a putative drug against a B cell malignancy, the method comprising:

(a) treating a model animal having a B cell malignancy with a test agent; and (b) detecting B cell malignancy cells in a peripheral tissue versus in a bone marrow of the model animal treated as in (a), wherein an increase in the ratio as compared to the ratio prior to the treatment is indicative that the test agent is a putative drug against the B cell malignancy.

According to some embodiments of the invention, the test agent is an anti CD84 antibody.

According to some embodiments of the invention, the model animal is selected from the group consisting of a xenograft model induced by transplanting human CLL in mice and the Eu-TCL1 murine model.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are scatter plots showing the ability of the blocking anti-CD84 antibody of hybridoma B4 to induce CLL cell death. FIGS. 1A-B—$1 \times 10^7$ CLL cells were incubated with anti-CD84 from the B4 hybridoma (5 μg/ml), or a control antibody (IgG2a). 24 h later, CLL cell death was analyzed by Annexin 7AAD staining. Presented are representative plots out of 10 independent experiments. FIGS. 1C-D—$1.6 \times 10^6$ CLL cells were co-cultured with $1 \times 10^5$ M210B4, in the presence or absence of the anti-CD84 from the B4 hybridoma (5 μg/ml), or a control antibody. Following 48 h, CLL cell death was determined with Annexin 7AAD staining. Presented are representative plots out of 3 independent experiments.

Figure 2A:
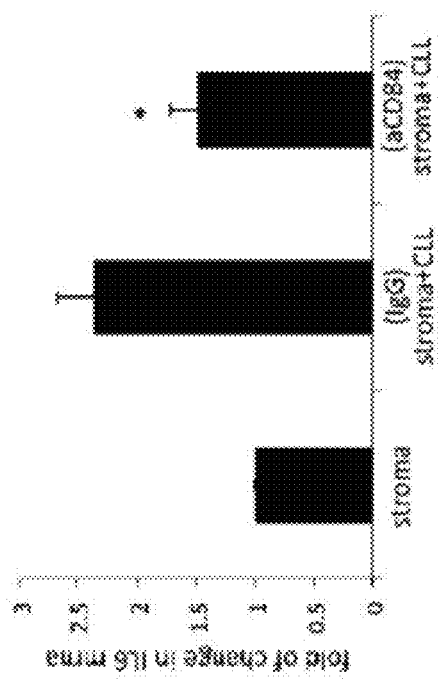
Figure 2B:
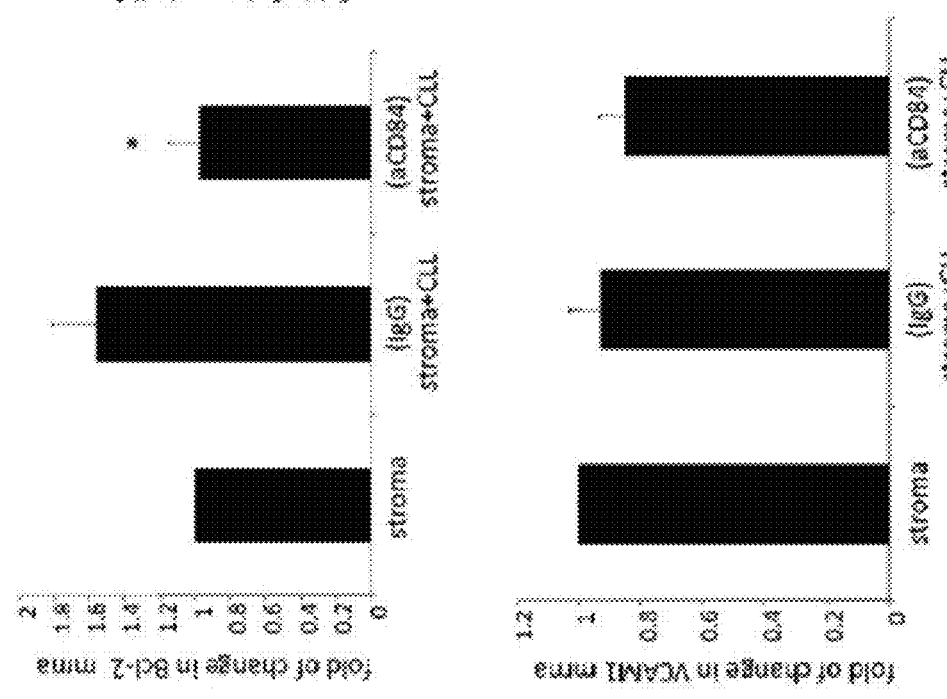
Figure 2C:
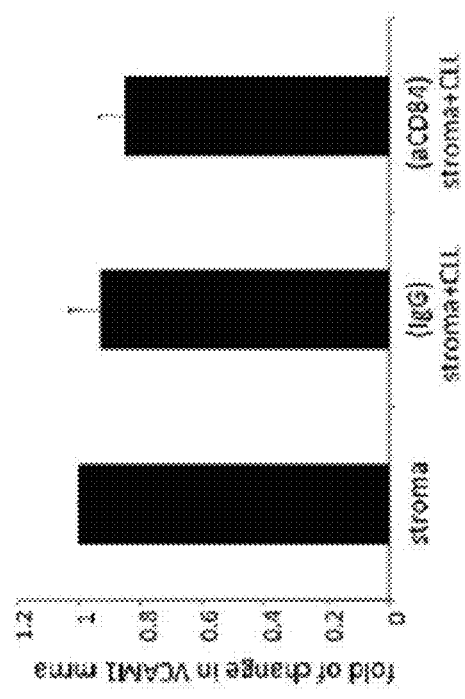

FIGS. 2A-C are bar graphs showing the ability of the anti-CD84 from the B4 hybridoma to mediate an anti-apoptotic effect on M210B4 bone marrow stromal cells in co cultures. In addition, homophilic interactions of CD84 expressed on CLL and stroma cells cause cytokine secretion from the stroma in order to further support the survival of CLL cells. M210B4 cells ($1\times10^5$) were co cultured with CLL cells in the presence or absence of the anti-CD84 from the B4 hybridoma or an isotype control antibodies. 48 h later, cells were harvested and Bcl-2, IL-6 and VCAM-1 mRNA levels were analyzed by qRT-PCR. Results presented are a summary of n independent experiments and are expressed as a fold of change in expression in co-cultured M210B4 cells compared to co-cultured cells blocked for CD84 and to M210B4 cells (stroma only), which was defined as 1. (FIG. 2A) Fold of change in expression of Bcl-2, n=4, P=0.037 (FIG. 2B) fold of change in expression of IL6, n=5, P=0.037 (FIG. 2C) fold of change in expression of VCAM-1 n=6, P=0.25.

Figure 3:
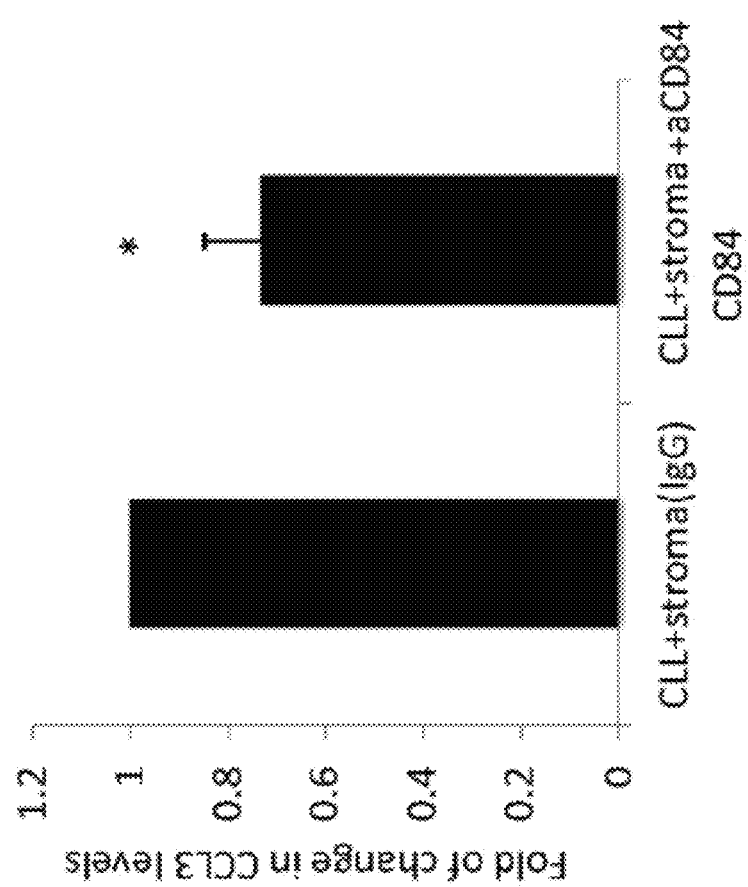

FIG. 3 is a bar graph showing that CD84 regulates CCL3 secretion in co cultures. $1.6\times10^6$ CLL cells were cultured with $1\times10^5$ M210B4 cells in the presence or absence of the anti-CD84 from the B4 hybridoma or an isotype control antibody (5 µg/ml). 48 h later, CCL3 level in the conditioned medium was analyzed by ELISA. Graphs show fold of change in CCL3 levels following CD84 blockage. The graph summarizes 6 experiments, *P=0.02.

FIGS. 4A-H show that the antibodies of some embodiments of the invention are superior in killing B-CLL cells as compared to the F8 antibody, as determined by Magic Red apoptosis assay. FIGS. 4A-D—Purified CLL cells were cultured in 24-well plates at a density of $1\times10^7$ cells/well in RPMI medium supplemented with 10% FCS, 2 mM glutamate, 100 U/ml penicillin, 100 µg/ml streptomycin, with or without supernatant derived from anti-CD84 hybridoma (F8/B1/B4) or control hybridoma for 24 h. Cells were centrifuged, washed and incubated with Magic Red (Immunochemistry Technology) according to the manufacturer's instructions, at 37° C. for 1 h. Then, Magic Red staining was measured by FACS analysis. FIGS. 4E-H—Ramos cells were cultured in 24-well plates at $1\times10^7$ cells/well in RPMI medium supplemented with 10% FCS, 2 mM glutamate, 100 U/ml penicillin, 100 µg/ml streptomycin, with or without supernatant derived from anti-CD84 hybridoma (F8/B1/B4) or control hybridoma for 24 h. Cells were centrifuged, washed and incubated with Magic Red (Immunochemistry Technology) according to the manufacturer's instructions, at 37° C. for 1 h. Then, Magic Red staining was measured by FACS analysis.

Figure 5B:
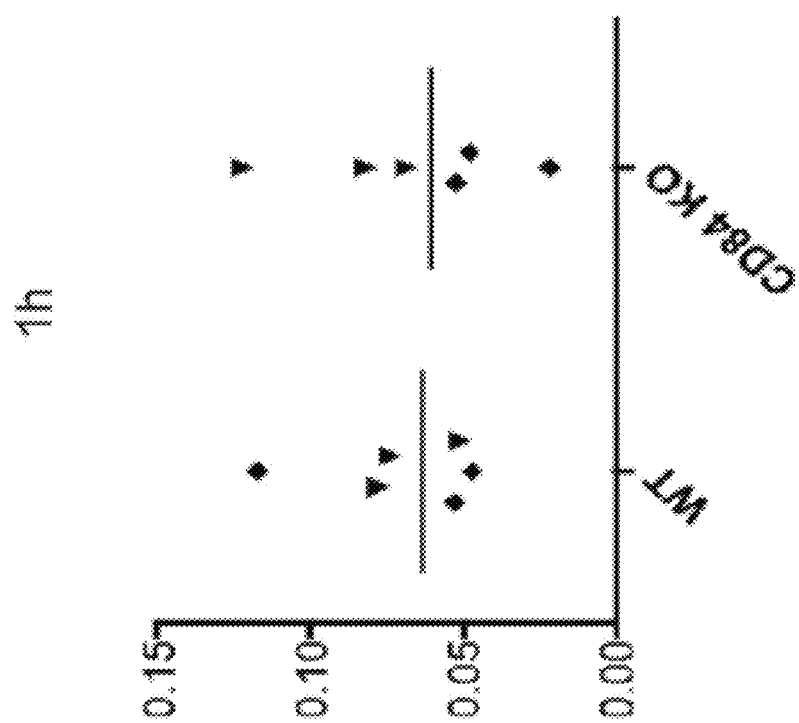
Figure 5A:
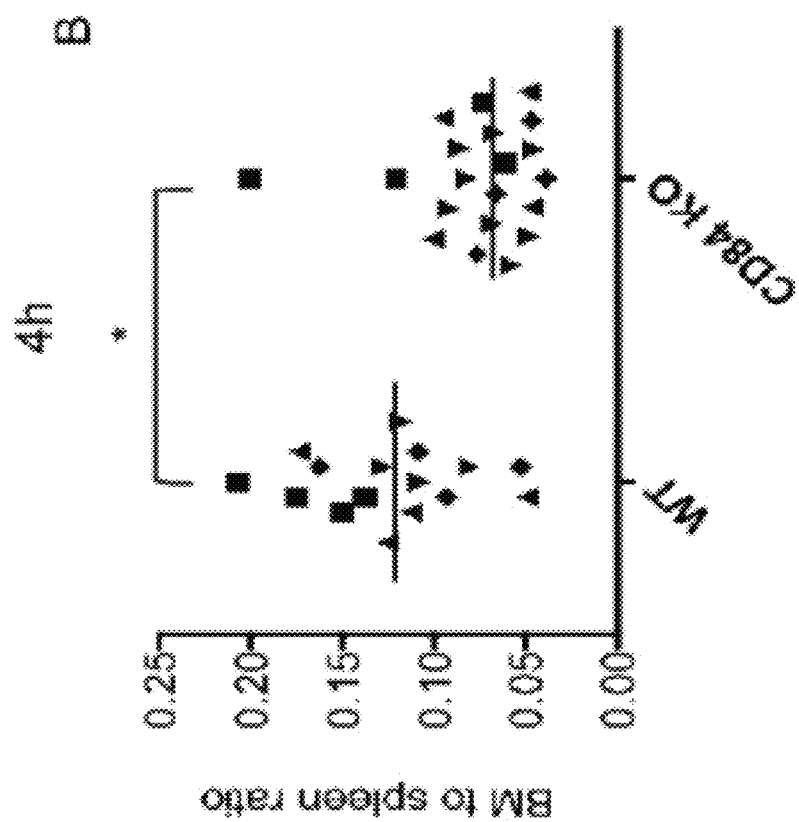

FIGS. 5A-B are scatter plots showing reduced number of CLL cells in BM of CD84KO mice. $1\times10^7$ CLL cells were stained with CFSE and injected i.v. into C57BL/6 WT or CD84KO mice. After 1 h (FIG. 5B) and 4 h (FIG. 5A), mice were sacrificed and number of CLL cells in spleens and BM were analyzed by FACS. The graphs show the ratio of labeled cells recovered from the BM to number of cells recovered from the spleens of (FIG. 5A) 16 mice in each group. *P=0.0005 or (FIG. 5B) 6 mice in each group, no statistical significant difference between groups.

Figure 6E:
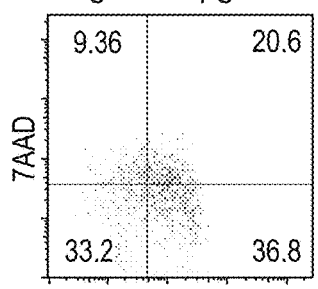
Figure 6F:
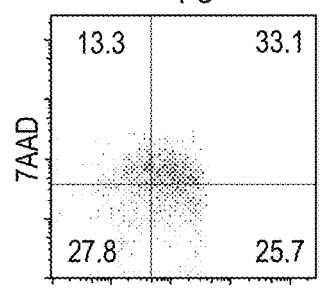
Figure 6G:
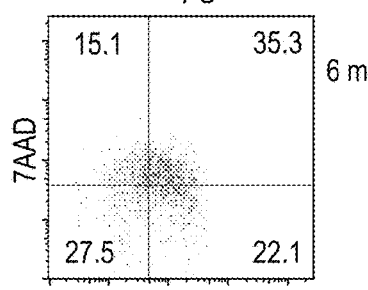
Figure 6H:
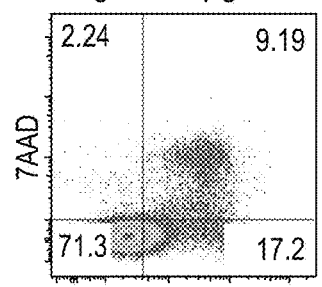
Figure 6I:
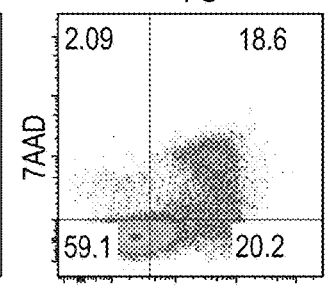
Figure 6J:
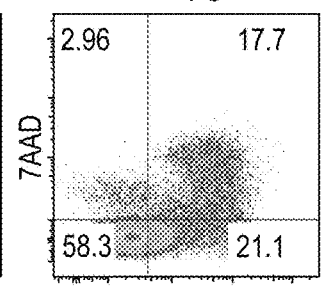
Figure 6K:
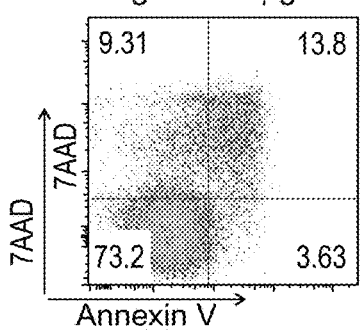
Figure 6L:
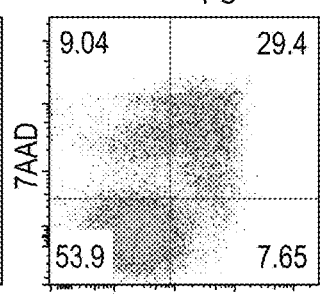
Figure 6M:
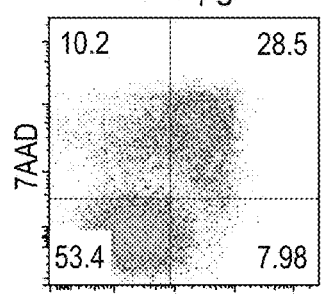

FIGS. 6A-M show that B1 and B4 antibodies recognize murine cells derived from TCL-1 mice. FIG. 6A is a histogram showing CD84 expression (black line) or staining with an isotype matched control antibody (grey line) on B220+CD5+cells derived from TCL-1 mice; FIGS. 6B-D are dot plots showing the percent of the B220+CD5+ in splenic cells derived from 18, 11 and 6 months old TCL-1 mice; and FIGS. 6E-M are dot plots. $1\times10^7$ B220+CD5+ cells derived from splenic TCL-1 mice were incubated with the B1 or the B4 or an isotype matched control (IgG2a) antibodies. 48 h later, cell death was analyzed by Annexin-7AAD staining.

Figure 7B:
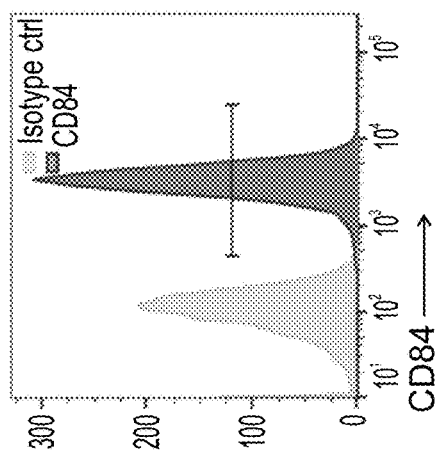
Figure 7D:
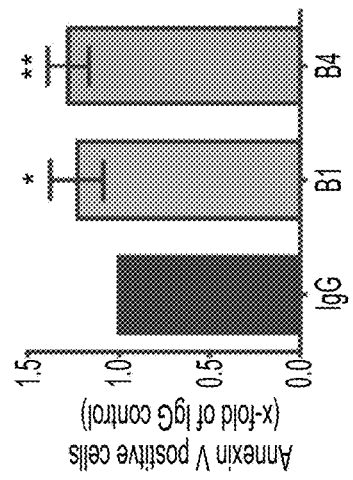
Figure 7A:
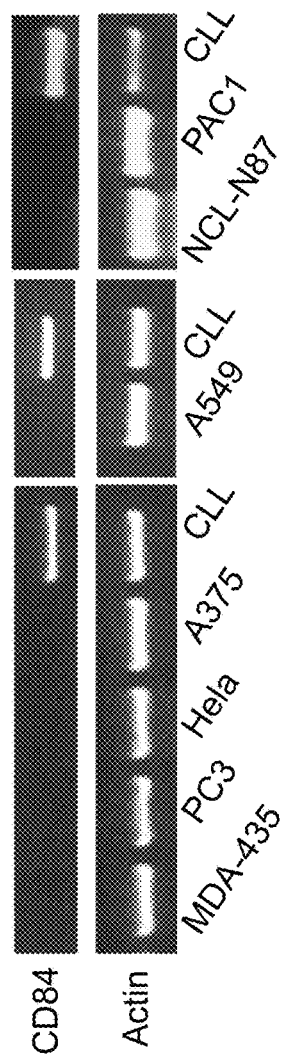
Figure 7C:
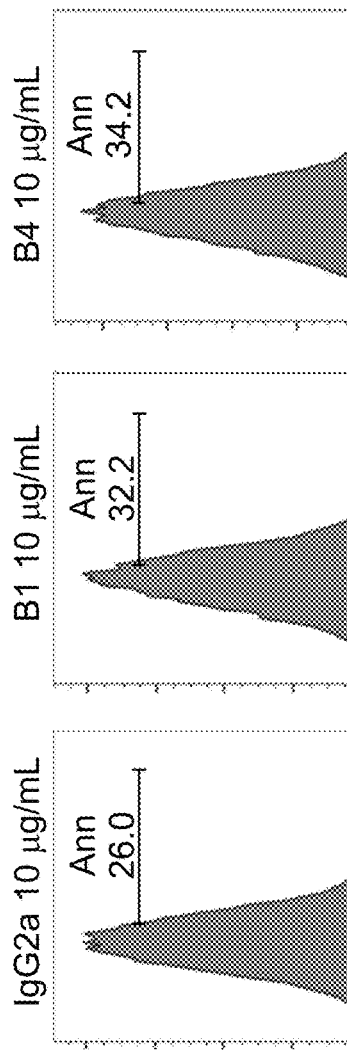

FIGS. 7A-D show evaluation of the therapeutic potential of the B1 and B4 antibodies in different tumor cell lines. FIG. 7A illustrate mRNA levels of CD84 and actin which were analyzed in different solid tumors: MDA435 (Human breast cancer), PC-3 (Human prostate cancer), Hela (Human cervical cancer), A375 (Human malignant melanoma), A549 (Human lung adenocarcinoma), PAC1 (Human Pancreas cancer) and N87 (Human gastric cancer); FIG. 7B is a histogram showing CD84 expression (black line) or staining with an isotype matched antibody (grey line) on Daudi cells; FIGS. 7C-D show $1\times10^7$ Daudi cells which were incubated with the B1 or the B4 antibody, or a control antibody (IgG2a). 48 h later, cell death was analyzed by Annexin-7AAD staining. The graph summarizes 7 independent experiments, showing fold of change in Annexin positive cells compared to Daudi cells incubated with an isotype matched control antibody.

FIGS. 8A-F show an elevated expression of CD84 in CLL cells. (FIG. 8A) B cells derived from healthy subjects (normal; N=4), as well as early- (N=6) and advanced- (N=6) stage CLL patients were purified and examined for CD84 expression. CD84 and actin mRNA were analyzed by RT-PCR; (FIG. 8B) qRT-PCR was performed using primers for CD84 and RP-2. Results are expressed as fold-change in CD84 mRNA in CLL cells compared to normal B cells, which was defined as 1. The graph summarizes results of three normal donors, and seven CLL patients; (FIGS. 8C-E) Histograms showing CD84 expression (grey line) or staining with secondary Ab alone (dotted line) in normal B cells and CLL cells. The graphs summarize the results of 4 normal donors and 18 CLL patients in percent or MFI; (FIG. 8F) Dot plots show CD84 and CD5 expression on CD19 positive cells normal (N=3) and CLL (N=4) cells.

FIGS. 9A-J show that B1 and B4 antibodies do not induce apoptosis in normal B cells. $1\times10^7$ B220+ splenic cells derived from 6, 8 and 11 months old C57BL/6 mice were incubated with the B1 or the B4 or a control (IgG2a) antibodies. 48 h later, cell death was analyzed by Annexin-7AAD staining. Graphs summarize 3 independent experiments, showing fold of change in the live B220+ cells incubated with B 1, B4 or an isotype matched control antibody.

FIGS. 10A-B show that CD84 is expressed on stroma cells. (FIG. 10A) CLL, NLC and M210B4 cells were purified and examined for CD84 expression. CD84 and actin mRNA were analyzed by RT-PCR; (FIG. 10B) Histograms show CD84 expression (black line) or staining with secondary Ab alone (grey line) in CLL, NLC and M210B4 cells.

FIGS. 11A-G show that CD84 expressed on stroma cells regulate survival of CLL cells. (FIGS. 11A-C) $1.6\times10^6$ CLL cells were co-cultured with $1\times10^5$ M210B4, in the presence or absence of the anti-CD84 B4 hybridoma (5 µg/ml), or a control antibody. After 24 h CLL cell death was determined with Annexin 7AAD staining. Presented are representative plots out of 3 independent experiments; (FIGS. 11D-G) siRNA (ON-TARGETplus SMARTpool, Human CD84 (NM_003874), Dharmacon) for CD84 or a control scrambled siRNA was transfected into $0.625\times10^5$ M210B4 cells. 18 h later $1\times10^6$ CLL cells were added to the culture. 48 h later, CLL cells were collected. Representative dot plots are demonstrated. Graph summarizes 9 independent experiments showing relative live CLL cells (average+standard error). *P=0.04, **P=3.1*10−10.

FIGS. 12A-D show that blocking CD84 on stroma with the B1 and B4 antibodies reduces survival of CLL cells. $0.625 \times 10^5$ M210B4 cells were incubated with the B1 or the B4 or a control antibody (IgG2a) antibodies. After 1 h, the antibodies were washed and $1 \times 10^6$ CLL cells were added. 48 h later cell survival was measured by Annexin-7AAD staining. The graph summarizes 3 independent experiments, showing fold of change in live CLL cells compared to CLL cells incubated with an isotype control antibody treated stroma.

DESCRIPTION OF SPECIFIC EMBODIMENTS OF THE INVENTION

The present invention, in some embodiments thereof, relates to anti CD84 antibodies, compositions comprising same and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Chronic lymphocytic leukemia (CLL) is characterized by the accumulation of CD5+ B lymphocytes in peripheral blood, lymphoid organs and bone marrow. The main feature of the disease is accumulation of the malignant cells due to decreased apoptosis. CD84 belongs to the signaling lymphocyte activating molecule family of immunoreceptors, and has an unknown function in CLL cells. The present inventors have previously shown that the expression of CD84 is significantly elevated from the early stages of the disease, and is regulated by macrophage migration inhibitory factor and its receptor, CD74. Activation of cell surface CD84 initiates a signaling cascade that enhances CLL cell survival. Both downmodulation of CD84 expression and its immune-mediated blockade induce cell death in vitro and in vivo. In addition, analysis of samples derived from an on-going clinical trial, in which human subjects were treated with humanized anti-CD74 (milatuzumab), shows a decrease in CD84 messenger RNA and protein levels in milatuzumab-treated cells. This downregulation was correlated with reduction of Bcl-2 and Mcl-1 expression. Thus, overexpression of CD84 in CLL is an important survival mechanism that appears to be an early event in the pathogenesis of the disease (Binsky-Ehrenreich et al. E. Pub. Feb. 25, 2013 Oncogene, WO2010/035259). These findings suggest novel therapeutic strategies based on the blockade of this CD84-dependent survival pathway.

The present inventors have now realized that homophilic interactions between CD84 expressed in B-CLL cells and stromal cells induce a survival signal in the cancer cells and independently retain the cells in the stromal environment of the bone marrow (see FIGS. 5A-B). The present inventors have further uncovered that CD84 is expressed on various types of lymphoma cells (FIG. 7B and FIG. 10A) as well as on different types of stromal cells. This suggests that CD84 might be involved in cell-cell interaction between CLL cells and their microenvironment (see FIG. 10A).

Thus, while screening for novel antibodies that block CD84-dependent survival pathway of CLL and induce mobilization of the CLL cells from the bone marrow, the present inventors have identified novel antibodies that induce apoptosis of CLL cells and protect against the anti-apoptotic activity and adhesive activity of stromal cells co-cultured therewith. Antibodies derived from the B1 and B4 hybridomas were able to downregulate secretion of CCL3 from CLL (Example 4) and induce apoptosis of purified CLL cells and Ramos cell line in a superior manner as compared to a previously isolated anti CD84 antibody described in WO2010/035259 (Example 5). These results place the present antibodies as important immunotherapy against CLL.

Thus, according to an aspect of the invention there is provided a method of identifying a putative drug against a B cell malignancy (e.g. B-CLL), the method comprising:

(a) treating a model animal having B cell malignancy (e.g. B-CLL) with a test agent; and (b) detecting B cell malignancy (e.g. B-CLL) cells in a peripheral tissue versus in a bone marrow of the model animal treated as in (a), wherein an increase in the ratio as compared to the ratio prior to the treatment is indicative that the test agent is a putative drug against B cell malignancy (e.g. B-CLL).

As used herein "a model animal having a B cell malignancy" refers to a mammal such as a non-human mammal which exhibits clinical manifestations of a B cell malignancy including B-CLL. The model may be a spontaneous model, a transgenic model or a xenograft model in which human B cell malignant cells (e.g. B-CLL cells) are transplanted.

Kurtova et al. Blood. 2009 Nov. 12; 114(20):4441-50 (herein incorporated by reference) describes several transgenic mouse models for B-CLL. Investigations of these mouse models revealed that deregulation of three pathways, Tcl1-Akt pathway, TNF-NF-kB pathway, and Bcl2-mediated anti-apoptotic pathway, result in the development of B-CLL. While deregulation of TCL1 alone caused a B-CLL phenotype in mice, overexpression of Bcl2 required aberrantly activated TNF-NF-kB pathway signaling to yield the disease phenotype.

According to a specific embodiment, the model animal is selected from the group consisting of a xenograft model induced by transplanting human CLL in mice and the Eu-TCL1 murine model.

As used herein "a test agent" refers to a molecule which decreases CD84 expression or activity. The test agent can be a small molecule, a nucleic acid silencing agent (e.g., siRNA or antisense), an antibody or a peptide (e.g., a soluble CD84 molecule which interferes with CD84 homophilic interactions, such as described in WO2010/035259).

According to a specific embodiment the test agent is an anti CD84 antibody.

Detection of malignant B cells (e.g. B-CLL cells) can be done using methods which are well known in the art and mainly depend on the model used.

Thus, when using the xenograft model, monitoring mobilization can be done by detecting human moieties in the mouse organs. Examples include, but are not limited to analyzing cell surface markers (human CD19) or pre-stained (CFSE+) cells.

Alternatively or additionally the human malignant B cells (e.g. B-CLL cells) can be stained (e.g., fluorescently, radioisotope staining) prior to transplantation for ease of detection.

Examples of peripheral tissues in which the amount of malignant B cells (e.g. B-CLL cells) can be monitored include, but are not limited to, spleen, peritoneal cavity, peripheral blood, lymph nodes and bone marrow (Durig J et al, Cancer Res 2007; 67: 8653-8661).

The ratio of malignant B cells (e.g. B-CLL cells) in a peripheral tissue versus in a bone marrow is compared to a control animal. A control animal may be the same animal prior to treatment or the same animal treated with a control agent (e.g., PBS or saline) which doesn't affect malignant B cell (e.g. B-CLL) mobilization.

As used herein an "increase" refers to a statistically significant increase. Thus the increase can be by at least 2, 5%, 10%, 20%, 50% or more.

Using the present methodology anti CD84 antibodies can be isolated.

Thus, according to an aspect of the invention there is provided an isolated antibody comprising an antigen recognition domain which specifically binds CD84 and,
(i) down regulates the anti-apoptotic activity of stromal cells on chronic lymphocytic leukemia (CLL) cells; and/or (i.e., additionally or alternatively)
(ii) induces mobilization of CLL cells from the bone marrow (to peripheral organ/tissues).

As used herein "down regulates" refers to a statistically significant reduction. Thus the decrease can be by at least 2, 5%, 10%, 20%, 50% or more.

As used herein "stromal cells" refers to adherent cells which reside in the bone marrow, also referred to as "marrow stromal cells". Examples of marrow stromal cell lines and primary stromal cell lines are provided herein below and in Kurtova et al. supra.

The reduction in the anti-apoptotic activity of stromal cells can be detected by reduction in survival factors such as IL-6 (in stroma), IL-8 (in stroma) and Bcl-2 (B-CL-2, which is reduced in both the stroma and CLL).

Thus, according to an aspect of the invention there is provided an isolated antibody comprising an antigen recognition domain comprising complementarity determining regions (CDR as set forth in SEQ ID NOs: 1, 2, 3, 4, 5 and 6 (B4), wherein the antibody specifically binds CD84.

According to a specific embodiment the isolated antibody comprises SEQ ID NOs: 4 (CDR1), 5 (CDR2) and 6 (CDR3), (sequentially arranged from N to C on a light chain of the protein) and 1 (CDR1), 2 (CDR2) and 3 (CDR3) (sequentially arranged from N to C on a heavy chain of the protein) (Clone B4).

Alternatively, there is provided an isolated antibody comprising an antigen recognition domain comprising complementarity determining regions as set forth in SEQ ID NOs: 7, 8, 9, 10, 11 and 12 (B1), wherein the antibody specifically binds CD84.

According to a specific embodiment the isolated antibody comprises SEQ ID NOs: 10 (CDR1), 11 (CDR2) and 12 (CDR3), (sequentially arranged from N to C on a light chain of the protein) and 7 (CDR1), 8 (CDR2) and 9 (CDR3) (sequentially arranged from N to C on a heavy chain of the protein) (Clone B1).

The antibodies of the present invention having the above-mentioned CDRs, are collectively referred to as "the anti-CD84 antibodies of the present invention".

As used herein the term "CD84" refers to an expressed isoform of the CD84 gene. Examples include but are not limited to Q9UIB8-1, Q9UIB8-2, Q9UIB8-3, Q9UIB8-4, Q9UIB8-5, Q9UIB8-6 and Q9UIB8-7.

According to a specific embodiment, the CD84 refers to CD84 isoform C, an isoform of CD84 which is assigned with Accession Numbers AF054815.1 NP_003865.1 (NM_003874, Q9UIB8-3) or SEQ ID NOs: 13 or 14.

The general affinity of the anti CD84 antibody is preferably higher than about, $10^{-6}$ M, $10^{-7}$ M, $10^{-8}$ M, $10^{-9}$ M, $10^{-10}$ M and as such is stable under physiological (e.g., in vivo) conditions.

According to a specific embodiment the affinity is preferably higher than (i.e., at least) about, $10^{-8}$ M or $10^{-9}$ M, e.g., $1\text{-}50\times10^{-9}$ M, $1\text{-}100\times10^{-9}$ M, $0.5\text{-}50\times10^{-9}$ M or $0.5\text{-}100\times10^{-9}$ M.

As used herein the term "isolated" refers to a level of purity such that the protein of the invention is the predominant form (e.g., more than 50%) in the preparation. In other words, other antibodies which are characterized by low or no affinity to CD84 (exceeding the above values) are altogether present in the preparation in less than 50% of the total antibody molecules of the preparation. According to a specific embodiment, the anti CD84 is isolated from the physiological embodiment e.g., from the body (e.g., human or animal). According to a specific embodiment, the term isolated also means isolated from a library, such as a phage display library or hybridoma lines or libraries.

The antibody of the present invention typically binds to the extracellular portion of CD84 (SEQ ID NO: 15).

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

According to a specific embodiment, the antibody is a monoclonal antibody of any subtype e.g., IgG, IgM, IgA etc. According to a specific embodiment the antibody is IgG1 or IgG4.

According to a specific embodiment, the antibody is an IgG2a (e.g., B4, B1) or IgG1 (e.g., B1). Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that the CDR sequences described herein can be implemented in a bispecific antibody configuration.

As used herein "bispecific" or "bifunctional" antibody, refers to an artificial hybrid antibody having two different heavy/light chain pairs and two different binding sites. Bispecific antibodies can be produced by a variety of methods including fusion of hybridomas. See e.g., Songsivilai and Lachmann (1990) Clin. Exp. Immunol. 79:315-321; Kostelny et al. (1992) J. Immunol. 148:1547-1553. The bispecific antibody may bind CD84 and another target which is expected to cooperate with CD84 in biological processes, such as apoptosis, or may increase specificity to the malignant B cell (e.g. B-CLL). Examples of such targets include, but are not limited to, CD74, CD19, CD5, SLAM family receptors (like NTB-A; SLAMF7). Alternatively or additionally, the bispecific antibody may bind CD84 at an epitope, which is distinctive of the epitope to which the B1 or B4 antibodies bind. Alternatively or additionally, the bispecific antibody may include the B1 and B4 CDRs.

According to a specific embodiment the antibody inhibits CD84 homophilic interactions.

As used herein "CD84 homophilic interactions" refer to the ability of CD84 to strongly self-associate with a Kd in the submicromolar range; the association is driven by the Ig-V domain, forming an orthogonal homophilic dimer. According to a specific embodiment the homophilic interactions are between the CD84 on the CLL and the CD84 on the stromal cells as well as between CD84 on CLL cells.

Methods of determining CD84 homophilic interactions include, but are not limited to siRNA of CD84 on the stroma, knockout mice of CD84. The CD84 homophilic interactions were demonstrated previously in [Yan et al., PNAS 2007].

It has been previously suggested that CLL cells are able to actively manipulate their microenvironment [Binder M et al, PLoS One. 2012. 5(12):e15992, Neil E Kay et al, Leuk Res. 2007 July; 31(7): 899-906 ]. Specifically, it has been shown that CLL cells induce anti-apoptotic effects on their stromal counterparts in culture. The CLL-stoma cell interaction induces the expression and secretion of specific cytokines (i.e IL-6, IL-8) from the stroma and induces the expression of specific adhesion molecules like ICAM-1, while the expression of other adhesion molecules remains unchanged (i.e VCAM-1) [Plander Metal, Annals of Hematology. 2011. 90(12):1381-90].

According to an alternative or an additional embodiment, the antibody is capable of down regulating the anti-apoptotic activity of stromal cells on chronic lymphocytic leukemia (CLL) cells as well as that of the CLL cells on the stromal cell.

As shown in the Examples section which follows, CLL cells cultured with stromal cells in the presence or absence of a CD84 antibody of some embodiments of the invention showed a reduction of the anti-apoptotic gene Bcl-2 (FIG. 2A) and the cytokine IL-6 (FIG. 2B) repeats. Incubation with CLL cells elevated Bcl-2 and IL-6 mRNA levels in stromal cells, while no change in VCAM-1 message were observed.

Interestingly, CD84 blockage reduced Bcl-2 (FIG. 2A) and IL-6 (FIG. 2B) message levels, while VCAM-1 levels were not affected by this blockage (FIG. 2C). Identification of changes in gene expression (mRNA level) or protein synthesis/secretion can be done using methods which are well known in the art. mRNA expression can be quantified by RT-PCR or real time quantitative PCR, secretion of cytokines can be detected using ELISA in culture medium.

As used herein the term "inhibiting" or "decreasing" refers to a statistically significant decrease in gene expression (e.g., Bcl-2) or protein secretion (e.g., IL-6, IL-8 or CCL3) by at least 10%, 20%, 30%, 40%, 50%, 60%, 80% or more.

Due to its ability to bind CD84 and inhibit its function (in at least one the modes described above), the anti CD84 antibody of some embodiments of the invention is also referred to as a "blocking antibody" or a "neutralizing antibody" and as such can be used in therapeutic applications.

Thus, according to an aspect of the invention, there is provided a method of inducing apoptosis in B cells of a subject having a B cell malignancy (e.g. B-CLL), the method comprising administering to the subject a therapeutically effective amount of the anti CD84 antibody as described herein, thereby inducing apoptosis in B cells of the subject.

Accordingly, the present teachings also contemplate a method of inducing apoptosis in CLL cells. The method comprising contacting the CLL cells with the antibody of the present invention (described above), thereby inducing apoptosis of the CLL cells.

According to an embodiment of this aspect of the invention, the method is effected in vivo.

According to an embodiment of this aspect of the invention, the method is effected ex vivo.

According to an embodiment of this aspect of the invention, the method is effected in-vitro.

As used herein "inducing apoptosis" refers to increasing the level of apoptosis in treated cells by at least 2%, 5%, 10%, 20%, 30%, 40%, 50%, 70% or even more.

Methods of determining apoptosis include but are not limited to, Annexin staining, and magic red staining. Specifics of such methods are described in the Examples section which follows.

According to another aspect there is provided a method of treating B-CLL in a subject in need thereof, the method comprising administering to the subject a therapeutically effective amount of the anti CD84 antibody as described herein, thereby treating B-CLL.

Yet according to another aspect there is provided use of the anti CD84 antibody as described herein in the manufacture of a medicament identified for the treatment of a B cell malignancy.

As used herein, the term "subject" or "subject in need thereof" refers to a mammalian e.g., human subject, male or female at any age, who has been diagnosed with a B cell malignancy.

As used herein the term "B cell malignancy" refers to a malignancy of hematopoietic or lymphoid tissues involving B lymphocytes of any subtype or stage of differentiation (e.g. early pre-B cells, pre-B cells, mature B cells, plasma cells).

According to one embodiment, the B cell malignancy comprises a lymphoma, a leukemia or a myeloma.

Such diseases include, but are not limited to, Hodgkin's Lymphoma, non-Hodgkin's Lymphoma, Diffuse large B-cell lymphoma (DLBCL), B-cell chronic lymphocytic leukemia (B-CLL)/chronic lymphoid leukemia (CLL), Chronic lymphocytic leukemia/small lymphocytic lymphoma, a chronic myelocytic leukemia (CML), an Extranodal marginal zone B-cell lymphoma—mucosa-associated lymphoid tissue lymphoma, a Follicular lymphoma, a Mantle cell lymphoma, a Nodal marginal zone B-cell lymphoma, a Burkitt's lymphoma, a Hairy cell leukemia, a Primary central nervous system lymphoma, a Splenic marginal zone B-cell lymphoma, a Lymphoplasmocytic lymphoma, a Primary mediastinal B-cell lymphoma, multiple myeloma, Acute lymphocytic leukemia (also known as acute lymphoblastic leukemia or ALL), acute lymphoblastic pre-B cell leukemia, plasma cell leukemia, pre-B cell leukemia (e.g. pre-B ALL), early pre-B cells ALL (e.g. early pre-B ALL) or pre-B acute lymphoblastoid leukemia.

According to one embodiment, the B cell malignancy is B-CLL.

As used herein the term "B-CLL" or "CLL" refers to an abnormal neoplastic proliferation of B-cells. CLL is considered to be identical to a disease called small lymphocytic lymphoma (SLL), a type of non-Hodgkin's lymphoma which presents primarily in the lymph nodes. The World Health Organization considers CLL and SLL to present different stages of the same disease [Chiorazzi N, Rai K R, Ferrarini M (2005). "Chronic lymphocytic leukemia". *N. Engl. J. Med.* 352 (8): 804-15].

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The antibodies of the present invention can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect (i.e., down regulation in CD84 activity or expression).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., a B cell malignancy including B-CLL) or prolong the survival of the subject being treated. In a specific embodiment, the therapeutically effective amount is sufficient to induce apoptosis of B cells of a B cell malignancy (e.g. induce apoptosis of B-CLL cells).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

A B-CLL animal model such as the NOD-SCID mouse chimera as described previously [Shimoni A, Marcus H, Canaan A, et al. A model for human B-chronic lymphocytic leukemia in human/mouse radiation chimera: evidence for tumor-mediated suppression of antibody production in low-stage disease. Blood. 1997; 89:2210-2218], can be used to determine therapeutic efficacy of the antibodies of the present invention in vivo. Human peripheral blood mononuclear cells from B-CLL patients at different stages of the disease are transferred by intraperitoneal injection. This system supports long term survival of the human tumor cells. Chimeric mice are treated with the antibodies of the present invention for different periods of time, and the effect on grafting of the cells and survival is then assessed.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide (tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

To improve therapeutic efficacy, antibodies of the present invention can be further administered along with conventional therapy for a B cell malignancy (e.g. for B-CLL) such as chemotherapy, radiotherapy, biological therapy e.g., immunotherapy or bone marrow transplantation.

Following is a non-limiting list of examples of conventional therapies for B-CLL.

Purine analogs—fludarabine or chlorambucil are generally used in this category of treatments. Monoclonal antibodies—Monoclonal antibodies such as alemtuzumab (directed against CD52) and rituximab (directed against CD20) are generally used in this category of treatments.

Combination chemotherapy—Combination chemotherapy options are typically used in newly-diagnosed and relapsed CLL. Recently, randomized trials have shown that combinations of purine analogues (fludarabine) with alkylating agents (cyclophosphamide) produce higher response rates and a longer progression-free survival than single agents: e.g., FC (fludarabine with cyclophosphamide); FR (fludarabine with rituximab); FCR (fludarabine, cyclophosphamide, and rituximab); CHOP (cyclophosphamide, doxorubicin, vincristine and prednisolone).

Allogeneic bone marrow (stem cell) transplantation—rarely used as a first-line treatment for a B cell malignancy (e.g. CLL) due to its risk. There is increasing interest in the use of reduced intensity allogeneic stem cell transplantation, which offers the prospect of cure for selected patients with a suitable donor.

The ability of the antibodies of the present invention to bind CD84 expressing B-CLL cells prompts their use in diagnostic applications.

Thus, according to an aspect of the invention there is provided a method of diagnosing a B cell malignancy (e.g. B-CLL) in a subject in need thereof, the method comprising:

(a) contacting a biological sample of the subject with the antibody of any one of claims 1-8 under conditions which allow the formation of immunocomplexes between CD84 isoform C (SEQ ID NO: 14) and said antibody; and (b) determining a level of said immunocomplexes in said biological sample, wherein an increase in level of said immunocomplexes beyond a predetermined threshold with respect to a level of said immunocomplexes in a biological sample from a healthy individual is indicative of the B cell malignancy (e.g. B-CLL).

As used herein the term "diagnosis" or "diagnosing" refers to classifying a pathology (e.g., cancer, e.g., B cell malignancy such as leukemia e.g., chronic lymphoid leukemia (CLL) e.g., B-CLL).

According to this aspect of the invention, the term "subject" or "subject in need thereof" refers to a mammalian e.g., human subject having a routine check-up or screen for the pathology, as well as to a subject who is at risk of having the pathology such as due to family history, environmental factors and/or a subject who exhibits suspicious clinical signs of the pathology. Some clinical signs of a B cell malignancy including B-CLL include but are not limited to predisposition to repeated infections such as pneumonia, herpes simplex labialis, and herpes zoster; enlarged lymph nodes; early satiety and/or abdominal discomfort which can be related to an enlarged spleen; mucocutaneous bleeding and/or petechiae which may be due to thrombocytopenia; tiredness and fatigue due to secondary to anemia; fevers, chills, and night sweats and weight loss; autoimmune hemolytic anemia.

As used herein the phrase "CD84 isoform C" refers to the isoform of CD84 which is assigned with Accession Numbers AF054815.1 NP_003865.1 (NM 003874, Q9UIB8-3). SEQ ID NOs: 13, 14.

Examples of "biological samples" include but are not limited to whole blood, serum, plasma, cerebrospinal fluid, urine, lymph fluids, and various external secretions of the respiratory, intestinal and genitourinary tracts, tears, saliva, milk as well as white blood cells, tissues, cell culture e.g., primary culture. According to a specific embodiment, the biological sample comprises B cells.

Malignant B cells (e.g. B-CLL cells) can be obtained from the blood, the bone marrow, the spleen, and/or the lymph nodes.

CD84 isoform C level can be determined at the protein level (level of expression and/or activity) or at the mRNA level (e.g., RT-PCR, real-time PCR etc.).

Following is a non-limiting list of examples of methods of determining a level of CD84C using the antibody of the present invention.

Enzyme linked immunosorbent assay (ELISA): This method involves a reaction between an enzyme and a substrate. A biological sample which comprises CD84C is put in a microwell dish. The CD84 specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate (anti CD84 antibody described herein is used), which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a CD84 specific antibody, as described herein, and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabeled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies i.e., CD84 antibody. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies, i.e., anti CD84 antibody as described herein. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

As mentioned an increase in the level of the CD84C beyond a predetermined threshold with respect to the level of same in a similar sample from a healthy individual is indicative of the disease (e.g., B-CLL).

As used herein, the phrase "biological sample from a healthy individual" refers to an unaffected control sample taken from a healthy subject (known not to have a B cell malignancy such as B-CLL) or from the same subject prior to the onset of the B cell malignancy e.g. B-CLL (i.e., healthy). Since biological characteristics depend on, amongst other things, species and age, it is preferable that the control saliva come from a subject of the same species, age. Alternatively, control data may be taken from databases and literature. It will be appreciated that the control sample may also be taken from the diseased subject at a particular time-point, in order to analyze the progression (i.e., monitoring) of the disease.

The term "increase" according to specific embodiment should be statistically significant.

Once diagnosis is made, the subject may be informed of the disease i.e., presence or absence of same and potential therapies for the B cell malignancy e.g. B-CLL.

To improve assay sensitivity, the method may further comprise corroborating the diagnosis using a diagnostic assay selected from surface marker expression distinctive of said CD84 isoform c, karyotype analysis and germline mutations.

Following is a non-limiting list of such assays/markers which can be used to corroborate the diagnosis of a B cell malignancy such as B-CLL.

Cell surface markers—B-CLL lymphocytes typically show B-cell surface antigens, as demonstrated by CD19, CD20, CD21, and CD23 monoclonal antibodies. In addition, they express CD5, which is more typically found on T cells. Because normal CD5+ B cells are present in the mantle zone (MZ) of lymphoid follicles, B-CLL is most likely a malignancy of an MZ-based subpopulation of anergic self-reactive cells devoted to the production of polyreactive natural autoantibodies. B-CLL cells express extremely low levels of surface membrane immunoglobulin, most often immunoglobulin M (IgM) or IgM/IgD and IgD. Additionally, they also express extremely low levels of a single immunoglobulin light chain (kappa or lambda).

Genetic analysis—An abnormal karyotype is observed in the majority of patients with CLL. The most common abnormality is deletion of 13q, which occurs in more than 50% of patients. Individuals showing 13q14 abnormalities have a relatively benign disease that usually manifests as stable or slowly progressive isolated lymphocytosis.

The presence of trisomy 12, which is observed in 15% of patients, is associated with atypical morphology and progressive disease. Deletion in the short arm of chromosome 17 has been associated with rapid progression, short remission, and decreased overall survival in CLL. 17p13 deletions are associated with loss of function of the tumor suppressor gene p53. Deletions of bands 11q22-q23, observed in 19% of patients, are associated with extensive lymph node involvement, aggressive disease, and shorter survival.

More sensitive techniques have demonstrated abnormalities of chromosome 12. Forty to 50% of patients demonstrate no chromosomal abnormalities on conventional cytogenetic studies. However, 80% of patients will have abnormalities detectable by fluorescence in situ hybridization (FISH). Approximately 2-5% of patients with B-CLL exhibit a T-cell phenotype.

Investigations have also identified a number of high-risk genetic features and markers that include germline immunoglobulin variable heavy chain ($IgV_H$), $IgV_H$ V3-21 gene usage, increased CD38 expression, increased Zap70 expression, elevated serum beta-2-microglobulin levels, increased serum thymidine kinase activity, short lymphocyte doubling time (<6 mo), and increased serum levels of soluble CD23. These features have been associated with rapid progression, short remission, resistance to treatment, and shortened overall survival in patients with B-CLL.

Germline mutations—Germline $IgV_H$ has been shown to indicate a poor prognosis. Studies have shown that these patients also have earlier progression of B-CLL after treatment with chemotherapy. The use of certain $IgV_H$ genes, V3-21, have also been associated with poor prognosis regardless of $IgV_H$ mutational status.

For any of the above clinical purposes (diagnostic or therapeutic), the anti CD84 antibody of the present invention can be bound (conjugated or attached) to a pharmaceutical agent.

Accordingly, the antibody can be attached to a pharmaceutical agent.

As used herein a pharmaceutical agent can be a drug (used in therapy) or a detectable moiety.

Various types of detectable or reporter moieties may be conjugated to the proteins of the invention. These include, but not are limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

An affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

As used herein "drug" refers to a therapeutically active ingredient such as a small molecule (e.g., chemotherapy), a toxin, a protein, a lipid, a carbohydrate or a combination of same.

Alternatively or additionally, the proteins can be attached (or conjugated) to non-proteinacious moieties which increase their bioavailability and half-life in the circulation.

The phrase "non-proteinaceous moiety" as used herein refers to a molecule not including peptide bonded amino acids that is attached to the above-described protein. Exemplary non-proteinaceous and preferably non-toxic moieties which may be used according to the present teachings include, but are not limited to, polyethylene glycol (PEG), Polyvinyl pyrrolidone (PVP), poly(styrene comaleic anhydride) (SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

Thus, such non-proteinaceous non-toxic moieties may also be attached to the above mentioned proteins to promote stability and possibly solubility of the molecules.

Bioconjugation of such a non-proteinaceous moiety (such as PEGylation) can confer the proteins amino acid sequence with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the protein of the present invention (e.g., CD84 binding).

Bioconjugation of the protein with PEG (i.e., PEGylation) can be effected using PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsville, Ala.)]. If desired, many of the above derivatives are available in a monofunctional monomethoxyPEG (mPEG) form. In general, the PEG added to the CCL1 amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-AC is made under argon by reacting a DCM solution of the PEG-OH with acryloyl chloride and triethylamine (molar ratios: OH 1: acryloyl chloride 1.5: triethylamine 2, at 0.2 gram PEG/mL DCM). Such chemical groups can be attached to linearized, 2-arm, 4-arm, or 8-arm PEG molecules. It will be appreciated that the antibodies of the invention may be produced using recombinant DNA technology (where a polynucleotide encoding the antibody of the invention is introduced into an appropriate host cell where the antibody is synthesized. Exemplary sequences are provided in SEQ ID NOs: 26 and 27) or by chemical synthesis such as by solid phase techniques.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Experimental Procedures

Transfection and protein expression of secreted CD84-ECD: For expression and secretion of CD84-ECD protein (SEQ ID NO: 15), HEK 293T cells were plated in 175 cm$^3$ cell culture flasks to a final confluence of 75% 24 h before transfection. For transfection, 30 mL complete DMEM medium and 3 mL of DNA precipitate-containing solution were used. Cultures were incubated an additional 24 hours after transfection, and then the medium was changed to serum-free DMEM for 2 days. The conditioned medium was collected; centrifuged for 1 h at high speed to remove cells and debris, filtrated with 0.2 µm filter unit and protein purification from conditioned medium was done using FLPC (Nickel affinity chromatography). After binding of the protein to the Ni2+ column, it was washed and eluted with high concentrations of imidazole, which competes with the His6-tag and displaces the protein. After purification, concentrated samples from each purification step and from the different peaks were analyzed by SDS-PAGE followed by western blotting and Coomassie staining of the gel.

Size-exclusion chromatography (gel filtration): The pooled, concentrated fractions of the Ni2+ affinity chromatography were loaded onto a 16/60 Superdex 200 column (preparative grade) by injection into the FPLC system. The proteins were eluted at a flow rate of 5 mL/min with PBS.

Fractions were collected according to the UV absorption, and changes in pH of the elutes. After pooling and concentrating the different peak fractions, samples were analyzed by SDS-PAGE, followed by western blotting and Coomassie staining.

Protein identification by ESI-MS/MS: In order to verify the identity of the CD84-ECD protein, the presumptive band of the Coomassie-stained gel was excised and analyzed by proteolytic digestion followed by electrospray ionization mass spectrometry. The procedure was carried out by the Biological Service Unit at the Weizmann Institute.

Hybridoma protocol: CD84-ECD protein was purified (as described before) from conditioned medium derived from 293 cells transfected with the CD84-ECD construct. Mice were immunized with purified CD84-ECD over a period of 3 months. Following positive ELISA test bleeding for antibodies against CD84-ECD (the plates were coated with purified ECD-CD84), spleens were removed; lymphocytes were isolated (with HBSS) and fused with NSO cells (ratio of 1:5) together with polyethilenglycol (PEG). Hybridomas were selected with HAT (Hypoxantine Aminopterine Tymidine) medium and their supernatant was analyzed for recognition of CD84-ECD using ELISA assay [Ho M K, Springer T A. Methods Enzymol 1984; 108: 313-324].

ELISA for hybridoma subclass detection: Hybridomas were shown to be of the IgM, k class by commercial ELISA kit. Briefly, cell-free culture supernatants were harvested from hybridoma, and IgM, IgG3, IgG1, αb, αa, Δ,λ,κ levels were determined using an ELISA methods according to manufacturer's instructions (BD Bioscience).

Hybridoma activation/blocking: Hybridoma B1/B4/F8 was added to CLL cells growing in RPMI medium containing 10% (v/v) FCS incubated at 37° C. for 18 h (for RNA extraction) and 24 h (for protein extraction), with or without MIF stimulation.

CLL Patient population: B lymphocytes were taken from the peripheral blood of both healthy subjects (normal/control) and CLL patients who satisfied diagnostic and immunophenotype criteria for CLL, at various stages of the disease. Cells were provided by the Hematology Institute of Kaplan Medical Center and the Sourasky Medical Center, in accordance with the IRB of the hospital, as described previously [Haran M et al., Leukemia. 2004; 18:1948-1950]. The diagnosis of CLL was based on standard criteria and patients were staged according to the Rai staging system [Hallek M et al., Blood. 2008; 111:5446-5456].

Cell purification: B-lymphocytes were purified using a RosettSep antibody cocktail (StemCell Vancouver, BC, Canada) as previously described [Lantner F et al., Proc. Natl. Acad. Sci. U.S.A. 2007; 104:13408-13413]. Briefly, this method is based on negative selection of B cells. 50 µl of cocktail containing divalent antibodies targeted at non-B-cell antigens (CD3, CD2, CD16, CD56, and CD14) was added to each milliliter of whole blood. After an incubation of 20 min, an equal amount of PBS was added to the mixture and the cells were put on a Ficoll gradient, centrifuged and isolated from the ficoll by PBS washes. Cells were used fresh or viably frozen in fetal calf serum (FCS) plus 10% dimethyl sulfoxide (DMSO) for storage in liquid nitrogen. Frozen cells were cultured overnight in 5% $CO_2$ in RPMI with 10% FCS and antibiotics.

M210B4 cells: M2-10B4 cells were purchased from ATCC (ATCC® CRL-1972™). This cell line is a clone derived from bone marrow stromal cells from a (C57BL/6J×C3H/HeJ)F1 mouse. Cells were grown in RPMI-1640 Medium, supplemented with 10% FCS and penicillin-streptomycin-glutamine and cultured in 37° C. in 5 % $CO_2$.

Cells of solid tumors: MDA435 (Human breast cancer), PC-3 (Human prostate cancer), Hela (Human cervical cancer), A375 (Human malignant melanoma; CRL 1619), A549 (Human lung adenocarcinoma), PAC1 (Human Pancreas cancer; 39532) and NCL-N87 (Human gastric cancer) were purchased from ATCC. Cells were grown in DMEM Medium, supplemented with 10% FCS and penicillin-streptomycin-glutamine and cultured in 37° C. in 5% $CO_2$.

Daudi cells: The Burkitt's lymphoma cell line, Daudi, was purchased from ATCC (ATCC® CCL-213™). $1 \times 10^6$ Daudi cells were cultured in RPMI medium containing 10% FCS with different concentrations of the anti-CD84 antibodies B1 or B4 or with a control antibody. Following 48 hours, cell survival was examined using Annexing staining (as described below).

Antibodies: For FACS staining anti CD84-PE (CD84.1.21 Bio Legend). For blocking: LEAF™ Purified anti-human CD84 Antibody (CD84.1.21 Bio Legend).

Flow cytometry: Staining of CLL cells was performed as previously described [Binsky I et al., Proc. Natl. Acad. Sci. U.S.A. 2007; 104:13408-13413]. The following antibodies were used: CD-19 (MiltenyiBiotec, Auburn, Calif.), anti-CD74 (Santa Cruz), IgG1κ isotype control (MOPC-21, BD Biosciences), CD49d (9F10, BD Biosciences), anti-CD84 (Ab-2, 152-1D5 Labvision), followed by PE anti-mouse secondary antibody (Jackson ImmunoResearch Laboratories) or anti CD84-PE (CD84.1.21 Bio Legend), PE anti-human CCR1/CCR5 Antibody (BioLegend), PE anti-mouse IgM Antibody, RMM-1 (BioLegend), APC anti-mouse/human CD45R/B220 Antibody, RA3-6B2 (BioLegend), Anti-Mouse CD5 eFluor®, 450 53-7.3 (eBioscience). Staining was analyzed by FACSCanto (BD Biosciences).

Intracellular Staining for Bcl-2: Cells were permeabilized and fixed using BioLegend's FOXP3 Fix/Perm solution for 20 minutes in room temperature, than washed twice with cell staining buffer and again with BioLegend's FOXP3 Perm buffer. Next, cells were incubated with BioLegend's FOXP3 Perm buffer for 15 minutes in the dark and then stained for 30 min on ice with anti-PE anti-Bcl-2 Antibody (BCL/10C-4, Biolegend) or anti-isotype control. Cell staining was assessed in FACSCanto flow cytometer (BD Biosciences).

Cell death detection: Annexin and PI/7AAD staining: Purified CLL cells were cultured in 24-well plates at $1 \times 10^7$ cells/well in RPMI medium supplemented with 10% FCS, with or without 1.5-2 µg of anti-CD84 (ab-3202 Abcam/152-1D5 Thermo) followed by 0.5 µg of anti Fab (Jackson) or an IgG isotype control antibody (MOPC-21 BioLegend) for 24 and 48 h. Cells were centrifuged, washed, and stained with Annexin (BD Biosciences), and propidium iodide (PI; 25 µg/ml) (Sigma) or 7AAD (BD Biosciences) was added for 15 min at room temp in the dark. The extent of Annexin+ PI/7AAD staining was analyzed by FACSCanto (BD Biosciences).

Magic Red Apoptosis Detection Kit: $10^7$ CLL cells per ml were incubated at 37° C. for 1 h with Magic Red (Magic Red Caspase Detection Kit for caspase 3 and 7 MR-(DEVD)2 Immunochemistry Technology) according to the manufacturer's instructions. Then, Magic Red staining was measured by FACSCalibur (BD Biosciences) analysis.

Enzyme-linked immunosorbent assay (ELISA): CLL cells were cultured with anti CD84 agonist or blocking antibody or B4 hybridoma, as previously described for 48-72 h. Co-cultures of CLL cells and NLC/M210B4 cells were blocked for CD84 using an antagonist antibody or blocking hybridoma B4 as described before.

Cell-free cultures supernatants were then harvested and levels of hCCL3 and mIL6 were determined using an ELISA method according to manufacturer's instructions (Human CCL3/mouse IL6 ELISA DuoSet R&D systems).

Blocking CD84 in co-cultures of CLL and M210B4: $1 \times 10^5$ stromal cells were plated per well in 24-well plate. After 18 hr, $1.6 \times 10^6$ CLL cells were added into each well, in the presence or absence of anti-CD84 blocking antibody (5 μg/μl) or B4 hybridoma (2.5-5 μg/μl) or isotype control and co-cultured for another 48 hr for viability assay of CLL cells or 72 h for ELISA of CCL3.

CD84 blocking: was performed as previously described [Binsky-Ehrenreich et al. E. Pub. Feb. 25, 2013 Oncogene]. Briefly, $1 \times 10^7$ CLL cells were incubated in RPMI medium containing 0.1% (v/v) FCS at 37° C. for 3 h. Next, cells were resuspended in medium containing 2.5 μg of anti CD84 (CD84.1.21 BioLegend) or by B4 hybridoma 2.5-5 μg (see material and methods) and incubated at 37° C. for 18 h (for RNA extraction) and 24-72 h (for protein extraction, intracellular staining and ELISA).

Real-time reverse transcription-PCR analysis: Levels of mRNA of human CD84, Rp2, Bcl-2, CCL3, IL6, and VCAM were analyzed by quantitative real-time RT-PCR using a Light-Cycler instrument (Roche Diagnostics, Mannheim, Germany). The reaction volume (10 μl) contained 3 mM MgCl2, LightCycler HotStart DNA SYBR Green I mix (Roche Diagnostics), specific primer pairs, and 2.5 μl of cDNA. Conditions for PCR were as follows: 10 minutes at 95° C. followed by 40-60 cycles of 15 seconds at 95° C., 15 seconds at 60° C., and 15 seconds at 72° C. PCR was performed in duplicates as previously described [Luger D et al., J. Clin. Immunol. 2004; 24:579-590].

Primer sequences were as follows:
hBcl-2: 5'GGATCAGGGAGTTGGAAG3' GCACTGC-CAAACGGAG (SEQ ID NOS: 16-17, respectively).
hCCL3: 5'CGAGCAGCCAGTGCTCCAAGC 3'GGCT-GTTTGGCAACAACCAGT CCA (SEQ ID NOs: 18-19, respectively).
Mouse Bcl-2: 5' GCTACCGTCGTGACTT 3' GCCGGT-TCAGGTACTC (SEQ ID NOs: 20-21, respectively).
IL6 mouse: 5' CCACTTCACAAGTCGGAGGCT TA 3'GCAAGTGCATCATCG TTGTTCATAC (SEQ ID NOs: 22-23, respectively).
VCAM1 mouse: 5' TACCAGCTCCCAAAATCCTG 3'TCTGCTAATTCCAGCCTC GT (SEQ ID NOs: 24-25, respectively).
RP-2 levels were used to normalize samples for calculation of the relative expression levels of other genes.
CD84: 5'TTGTTCCGTTTGTTCAAGAG 3'CGGAATAAACTGTGTTCACTG$^h$ (SEQ ID NOs: 28-29, respectively).

Downregulation of CD84 by siRNA: ON-TARGETplus SMARTpool, Human CD84 (NM_003874), Dharmacon, was used for downregulation of CD84.

Mice: All animal procedures were approved by the Animal Research Committee at the Weizmann Institute.

TCL1 mice as a model for chronic lymphocytic leukemia: The percent of malignant population in various ages of TCL-1 mice were determined. Splenic cells were obtained from 18, 11, and 6 months old TCL-1 mice and were analyzed for their B220+CD5+ population by FACSCanto (BD Bioscience).

Splenic B cells were then incubated with anti-CD84 (B1 or B4) or an isotype matched control antibody in Iscove's medium containing 2% FCS for 48 h. Cell survival was analyzed by Annexin-7AAD staining (as described above).

Xenograft model for CLL: CLL cells were labeled with 5 μM carboxyfluorescein diacetate succinimidyl ester (CFSE; Anaspec) for 5 min at 37° C. CFSE had no effect on cell survival throughout the experiment. $1 \times 10^7$ cells then were i.v. injected into control C57BL/6 and CD84 KO mice. Homing of CLL cells to the spleen, BM and PB was determined 1 h and 4 h later by FACS analysis of isolated cells from tissues.

Normal B cells: Splenic B cells were obtained from 6, 8 and 11 months old C57BL/6 mice. Cells were isolated and stimulated with 5 μg/ml anti-CD84 B1 or B4 antibodies, and compared to the effect of an isotype matched control antibody.

Eμ-TCL1 model for CLL: Eμ-TCL1 transgenic mice were used to follow CLL progression by monitoring CD5$^+$ B lymphocytes expansion as previously described [Bichi R et al., Proc Natl Acad Sci USA. 2002. 99: 6955-6960]. Chimeric mice were generated by transplanting WT and CD84 KO mice with $5 \times 10^6$ BM cells from Eμ-TCL1 mice. After 4, 6, 8 and 13 months the peritoneal cavity, PB, Spleen and BM of the recipient mice were sacrificed and cells were extracted, stained for CD5 (450 53-7.3 (eBioscience), IgM (RMM-1 BioLegend), and B220 (RA3-6B2 (BioLegend) and analyzed by FACSCanto (BD Bioscience).

Example 2

The B4 Antibody Induces Apoptosis in CLL Cells

The present inventors have determined whether the B4 antibodies generated according to the present teachings are capable of inducing apoptosis in primary human CLL cells. As demonstrated in FIGS. 1A-D, the hybridoma-derived B4 antibody, induced cell death in CLL cells cultured alone (FIGS. 1A-B). As previously shown, different types of stromal cells, such as primary human Nurse like cells (NLC) and marrow stromal cells (MSC) (cell line M210B4, CRL-1972™) protect CLL cells in co-culture from apoptosis, and are an integral part of the CLL microenvironment (Burger J A et al., Blood. 2009. 114:3367-3375, Kurtova A V et al., Blood. 2009. 114:4441-4450). Interestingly, the B4 hybridoma-derived antibody overcame the protective effect of the stroma and induced CLL death when co-cultured with M210B4 cells (FIGS. 1C-D). Therefore B4 hybridoma, can be used as a blocking antibody. Measuring of apoptosis includes all annexin positive cells (single and double) annexin positive total population increases from 46.18% to 55.75%.

Example 3

CD84 Regulates an Anti-Apoptotic Effect on Bone Marrow Stromal Cells-B4

It has been previously suggested that CLL cells are able to actively manipulate their microenvironment [Binder M et al, PLoS One. 2012. 5(12):e15992, Neil E Kay et al, Leuk Res. 2007 July; 31(7): 899-906]. Specifically, it has recently been shown that CLL cells induce anti-apoptotic effects on their stromal counterparts in culture. The CLL-stoma cell interaction induces the expression and secretion of specific cytokines (i.e IL-6, IL-8) from the stroma and induces the expression of specific adhesion molecules like ICAM-1, while the expression of other adhesion molecules remains unchanged (i.e VCAM-1) [Plander M et al, Annals of Hematology. 2011. 90(12):1381-90].

To determine whether the CLL-stromal cells interaction mediated by CD84 induces a similar cascade in the stroma, CLL cells were cultured with M210B4 stomal cells in the presence or absence of a CD84 blocking hybridoma (B4) as described above (FIGS. 1C-D), and expression of the anti-apoptotic gene Bcl-2 (FIG. 2A), the cytokine IL-6 (FIG. 2B), and VCAM-1 (FIG. 2C) in M210B4 cells were monitored. Incubation with CLL cells elevated Bcl-2 and IL-6 mRNA levels in M210B4 cells, while no change in VCAM-1 message were observed.

Interestingly, CD84 blockage reduced Bcl-2 (FIG. 2A) and IL-6 (FIG. 2B) message levels, while VCAM-1 levels were not affected by this blockage (FIG. 2C).

Example 4

CD84 Regulates CCL3 Expression in Co Cultures-B4

It was previously shown that CLL cells are able to actively recruit cells and create a supportive microenvironment via the secretion of CCL3 [Zucchetto A et al., Cancer Res. 2009. 69(9):4001-4009. Burger J A et al., 2009. 113: 3050-3058]. Stimulation of CD84 expressed on CLL cells induces CCL3 expression and secretion (our non-published results). To directly demonstrate the regulatory role of CD84 in the CCL3 mediated secretion in CLL-stromal cells co-culture, CCL3 secreted levels were analyzed in the supernatants derived from CLL-stromal cells co-cultures, which were incubated in the presence or absence of a CD84 blocking hybridoma (B4) or an isotype control antibody. As demonstrated in FIG. 3, blocking of CD84 in CLL-M210B4 co-culture, downregulated the levels of human CCL3, derived from the CLL cells, secreted to the conditioned medium as detected by ELISA (FIG. 3).

Similarly, CCL3 secretion from CLL cells co-cultured with NLC cells in the presence or absence of anti-CD84 blocking antibody was analyzed. Blocking CD84 significantly downregulated secretion of CCL3 from CLL cells to the conditioned medium (data not shown). However, as NLC are of human origin, it was further verified that CD84 specifically regulates secretion of CCL3 from CLL cells in these co-cultures. Therefore CCL3 mRNA levels were analyzed in CLL cells cultured with NLC cells and demonstrated reduced expression of CCL3 message in CLL cells (data not shown).

Thus, CLL-microenvironment interaction is mediated by CD84, which promotes secretion of CCL3 from CLL cells.

Example 5

Comparison Between F8, B1 and B4 Antibodies

As shown in FIGS. 4A-H and in Table 1 below, antibodies of some embodiments of the invention (B1 and B4) were able to superiorly kill purified CLL cells, as demonstrated by higher percentage of apoptotic cells (FIGS. 4A-D), and Ramos (RA-1) Burkitt's lymphoma cells (ATCC CRL-1596™, FIGS. 4E-H) as compared to a blocking antibody described in the art (F8, PCT publication no. WO2010/035259).

TABLE 1

Comparison of apoptosis of CLL cells by F8, B1 and B4 antibodies

|    | Purified CCL (% apoptosis) | Ramos Cells (% apoptosis) |
|----|----------------------------|---------------------------|
| F8 | 34                         | 16                        |
| B1 | 73                         | 45                        |
| B4 | 75                         | 39                        |

Example 6

CD84KO Mice Show Decreased Number of Human CLL Cells in Their BM

In order to study the survival and the distribution of human CLL cells in the different compartments of transplanted mice, human primary CLL cells were fluorescently labeled with CFSE. The cells were then injected to CD84KO and WT mice. Following 4 hours, the number of cells residing in the different compartments was compared, and the ratio between the numbers of cells in the BM and the spleen of each mouse was calculated. As shown in FIGS. 5A-B, the ratio of CLL cells detected in the BM of the control mice was significantly reduced in CD84KO mice (FIG. 5A). In order to determine whether this phenomenon is a result of impaired arrival of the CLL cells to the BM compartment in CD84KO mice, or due to their inability to retain or survive in this compartment, CLL cells were injected to CD84KO or WT mice and the mobilization of cells to the BM was followed 1 hour after injection. As shown in FIG. 5B, homing of CLL cells to the BM after 1 hour was similar in WT and CD84 KO mice (FIG. 5B). This result might suggest that CLL cells home normally to the BM which lacks CD84 expression in the microenvironment. The reduced number of cells detected in the BM at a later time point is possibly due to the inability of the cells to retain or survive in the BM microenvironment in the absence of the CD84 signal.

Example 7

Evaluation of Species Cross Reactivity

Eμ-TCL1 a transgenic mouse model of CLL disease was used. In Eμ-TCL1 transgenic mice, there is an accumulation of B220 low IgM+CD5+ B lymphocytes in the peritoneal cavity, peripheral blood, bone marrow and lymphoid organs of the mice. The IgM+CD5+ B lymphocytes express CD84 on their surface (FIG. 6A).

It was then determined whether blocking CD84 activity with the B1 and B4 antibodies induced cell death. First, the percent of the malignant population in various ages of TCL-1 mice were determined. Splenic cells derived from 18, 11, and 6 months old TCL-1 mice were analyzed for their B220+CD5+ population by FACS. While most splenic cell from the 18 and 11 months old TCL-1 mice were the malignant cells (B220+CD5+), the B220+CD5+ population could hardly be detected in spleens derived from 6 months old TCL-1 mice (FIGS. 6B-D). Next, the effect of the antibodies on cell survival was followed. The malignant splenic B cells were incubated with anti-CD84 (B1 or B4) or an isotype matched control antibody in Iscove's medium containing 2% FCS. 48 h later cell survival was analyzed by Annexin-7AAD staining. As can be seen in FIGS. 6E-M, blocking CD84 with B1 and B4 antibodies induced apoptosis in the malignant B220+CD5+ population. Surprisingly, survival of peripheral non-malignant B220+CD5– B cell population was not affected by this treatment (as described in FIGS. 9A-J). These results suggest that the anti human CD-84 antibodies, B1 and B4, can block murine CD84 on malignant mouse cells and reduce their survival.

Example 8

Analysis of CD84 Expression on Tumors

Various cell lines express CD84 as is illustrated in the website www(dot)broadinstitute(dot)org/ccle/. Most of the cell lines belong to the hematopoietic origin, however, a few solid tumors were selected to analyze CD84 expression. mRNA was extracted from different solid tumor cell line: MDA435 (Human breast cancer), PC-3 (Human prostate cancer), Hela (Human cervical cancer), A375 (Human malignant melanoma), A549 (Human lung adenocarcinoma), PAC1 (Human Pancreas cancer) and NCL-N87 (Human gastric cancer). CD84 message was analyzed by RT-PCR. As can be seen in FIG. 7A, CD84 mRNA was not detected in any of these cells.

Analysis of the CD84-induced cascade in CD84 expressing hematopoietic tumor cells was carried out in the Burkitt's lymphoma cell line, Daudi. As can be seen in FIG. 7B, Daudi cells express CD84 on their cell surface.

Next, the effect of the anti-CD84 B1 and B4 antibodies on apoptosis induction in Daudi cells was determined. Daudi cells were cultured with different concentrations of the anti-CD84 antibodies B1 or B4 or with a control antibody. Following 48 hours, cell survival was examined using Annexing staining. Blocking CD84 induced death of the Daudi cells (a representative concentration is shown in FIG. 7C).

Example 9

Analysis of CD84 Expression and Function in Normal Tissues

Various normal tissues express CD84 as is illustrated in the website www(dot)gtexportal(dot)org/home/. As shown therein, CD84 is expressed mainly on EBV transformed cells and in the spleen.

The role of CD84 as a survival receptor in normal tissues was analyzed. CD84 expression levels in healthy and CLL cells from patients at various disease stages were compared. Purified B cells from healthy subjects as well as early- and advanced-stage CLL cells were analyzed for the presence of CD84 mRNA (targeting a segment common to all isoforms). As shown in FIGS. 8A-B, low levels of CD84 mRNA were detected in normal B cells, while elevated levels of CD84 mRNA were observed in all the CLL patients, regardless of disease stage.

In addition, CD84 cell surface levels were significantly higher in all CLL cells when compared to total (FIGS. 8C-E) or CD5+ normal B cells (FIG. 8F). Thus, normal B cells express CD84 at lower levels.

Next, the effect of anti-CD84 B1 and B4 antibodies on survival of normal B cells was evaluated. Splenic B cells derived from 6, 8 and 11 months old C57BL/6 mice were isolated and stimulated with 5 µg/ml anti-CD84 B1 or B4 antibodies, and compared to the effect of an isotype matched control antibody. As can be seen in FIGS. 9A-J, both B1 and B4 had no effect on the viability of peripheral normal B cells. These results suggest that while B1 and B4 antibodies can block murine CD84 activity on malignant mouse cells and reduce cell survival (FIG. 6C), they do not induce apoptosis in normal B cells.

Example 10

Analysis of CD84 Expression in the Tumor Microenvironment

CD84 expression on marrow stromal cells (MSCs) and nurse like cells (NLC) present in the tumor microenvironment was followed. For MSCs, primary bone marrow MSCs derived from CLL patients were used, these cells were isolated and cultured as previously described [Kay et al., Leukemia Research 31, 899-906 (2007)] and murine MSC lines (M210B4) F1 mouse were also used. These cell lines were shown to protect CLL cells from spontaneous and drug-induced apoptosis [Kurtova et al., Blood 114, 4441-4450 (2009)]. NLC were isolated and cultured as described previously [Burger et al., Blood 96, 2655-2663 (2000)].

As previously shown CD84 mRNA was detected in CLL cells (FIG. 10A). In addition, CD84 mRNA was detected in M210B4 cells as well as in NLC (FIG. 10A). Next, CD84 expression was analyzed on the surface of these cells. As shown in FIG. 10B, in addition to its expression on CLL cells, CD84 was detected on the surface of NLC as well as M210B4 stromal cells. This suggests that CD84 might be involved in cell-cell interaction between CLL cells and their microenvironment.

Example 11

Analysis of the Role of CD84 in the Regulation of Microenvironment-induced Protection from CLL Spontaneous and Drug-induced Apoptosis To determine whether CD84 plays a role in the interaction of CLL cells with their microenvironment which results in cell survival, CLL cells were co-cultured with stroma cells (as described above) in the presence or absence of anti-CD84 blocking antibodies. M210B4 (FIGS. 11A-G) induced an anti-apoptotic effect on CLL cells, as measured by Annexin-PI/7AAD staining (described in detail in Example 1 above). Blocking of CD84, by the hybridoma B4 (FIGS. 11A-C), partially overcame the anti-apoptotic effect induced by the stroma, resulting in induction of CLL cell death.

The present inventors next wanted to determine whether the apoptosis induced by blocking CD84 was a direct effect on CLL cells, or if the antibodies could prevent the interaction of the CLL cells with the stroma, thereby inducing their death. Thus, CD84 expression was downregulated in M210B4 cells by siRNA. CLL cells were then added to the culture and their survival was monitored. As demonstrated in FIG. 11D-G, deletion of CD84 specifically reduced the stroma-mediated survival of CLL cells. Thus, CD84 expressed on the stroma mediates survival of CLL cells via cell to cell contact. To further demonstrate the role of CD84 expressed on the microenvironment on survival of CLL cells, CD84 expressed on M210B4 was blocked by the B1 and B4 antibodies. After 1 hour, the antibodies were washed and CLL cells were then added to the co-culture. 48 hours later cell survival was measured by Annexin-7AAD staining. Blocking of stromal CD84 significantly induced apoptosis of CLL cells (FIGS. 12A-D), suggesting that the survival induced by the stroma is mediated by CD84 stromal-CLL interaction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated antibody comprising an antigen recognition domain comprising:
   complementarity determining regions as set forth in SEQ ID NOs: 1, 2, 3, 4, 5 and 6 (B4); or
   complementarity determining regions as set forth in SEQ ID NOs: 7, 8, 9, 10, 11 and 12 (B1),
   wherein the antibody specifically binds CD84.

2. The isolated antibody of claim 1, down regulating the anti-apoptotic activity of stromal cells on chronic lymphocytic leukemia (CLL) cells.

3. The isolated antibody of claim 1, inhibiting the secretion of CCL3 from CLL cells.

4. The isolated antibody of claim 1, inhibiting the expression of BCL-2 in CLL.

5. The isolated antibody of claim 1, inhibiting the expression of stroma BCL-2.

6. The isolated antibody of claim 1, reducing the expression of IL-6 and IL-8 in stromal cells.

7. The isolated antibody of claim 1, inducing mobilization of CLL cells from the bone marrow.

8. The isolated antibody of claim 1, being an IgG.

9. The isolated antibody of claim 1, wherein the antibody is a humanized antibody or a chimeric antibody.

10. The isolated antibody claim 1, wherein the antibody is a bispecific antibody.

11. A pharmaceutical composition comprising the isolated antibody of claim 1 and a pharmaceutically acceptable carrier or diluent.

* * * * *